US012697062B2

(12) United States Patent
Le et al.

(10) Patent No.: US 12,697,062 B2
(45) Date of Patent: Aug. 4, 2026

(54) NOISE-ROBUST SLEEP APNEA DIAGNOSTIC SYSTEM AND RELATED METHOD

(71) Applicant: UNIVERSITY OF SOUTH FLORIDA, Tampa, FL (US)

(72) Inventors: Trung Quoc Le, Tampa, FL (US); Phat Kim Huynh, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 336 days.

(21) Appl. No.: 18/506,896

(22) Filed: Nov. 10, 2023

(65) Prior Publication Data

US 2024/0315641 A1 Sep. 26, 2024

Related U.S. Application Data

(60) Provisional application No. 63/488,021, filed on Mar. 2, 2023.

(51) Int. Cl.
A61B 5/00 (2006.01)
A61B 5/024 (2006.01)
A61B 5/346 (2021.01)

(52) U.S. Cl.
CPC ........ A61B 5/4818 (2013.01); A61B 5/02405 (2013.01); A61B 5/346 (2021.01); A61B 5/7203 (2013.01); A61B 5/726 (2013.01)

(58) Field of Classification Search
None
See application file for complete search history.

(56) References Cited

U.S. PATENT DOCUMENTS

2012/0123232 A1* 5/2012 Najarian ................. G16Z 99/00
600/407
2015/0230750 A1* 8/2015 McDarby ................. A61B 5/05

OTHER PUBLICATIONS

Abarbanel, Henry Di, et al. "The analysis of observed chaotic data in physical systems." Reviews of modern physics 65.4 (1993): 1331.
Atri, Roozbeh, et al. "Obstructive sleep apnea detection using spectrum and bispectrum analysis of single-lead ECG signal." Physiological measurement 36.9 (2015): 1963.
Bessaih, Hakima, et al. "Strong solutions to stochastic hydrodynamical systems with multiplicative noise of jump type." Nonlinear Differential Equations and Applications NoDEA 22.6 (2015): 1661-1697.
Brunton, Steven L., et al. "Chaos as an intermittently forced linear system." Nature communications 8.1 (2017): 19.
(Continued)

*Primary Examiner* — Ankit D Tejani
(74) *Attorney, Agent, or Firm* — HUSCH BLACKWELL LLP

(57) ABSTRACT

Methods and systems for obstructive sleep apnea diagnosis and prediction are disclosed. The methods and systems include: obtaining a white noise contaminated sensor signal for a patient; extracting a feature based on the white noise contaminated sensor signal; determining a matrix based on the feature; determining an intermittent forcing signal based on the matrix; determining an overcomplete representation of the intermittent forcing signal; and generating an obstructive sleep apnea indication based on the overcomplete representation and a threshold. Other aspects, embodiments, and features are also claimed and described.

20 Claims, 17 Drawing Sheets

(56) References Cited

OTHER PUBLICATIONS

Brunton, Steven L., et al. "Koopman invariant subspaces and finite linear representations of nonlinear dynamical systems for control." PloS one 11.2 (2016): e0150171.

Brunton, Steven L., et al. "Data-driven science and engineering: Machine learning, dynamical systems, and control." Cambridge University Press, 2022.

Brunton, Steven L., et al. "Discovering governing equations from data by sparse identification of nonlinear dynamical systems." Proceedings of the national academy of sciences 113.15 (2016): 3932-3937.

Byun, Sangwon, et al. "Detection of major depressive disorder from linear and nonlinear heart rate variability features during mental task protocol." Computers in biology and medicine 112 (2019): 103381.

Champion, Kathleen P., et al. "Discovery of nonlinear multiscale systems: Sampling strategies and embeddings." SIAM Journal on Applied Dynamical Systems 18.1 (2019): 312-333.

Chang, Yu-Ming, et al. "Heart rate variability as an independent predictor for 8-year mortality among chronic hemodialysis patients." Scientific reports 10.1 (2020): 881.

Contoyiannis, Y. F., F. K. Diakonos, and A. Malakis. "Intermittent dynamics of critical fluctuations." Physical review letters 89.3 (2002): 035701.

Donnelly, Lane F., et al. "Causes of persistent obstructive sleep apnea despite previous tonsillectomy and adenoidectomy in children with down syndrome as depicted on static and dynamic cine MRI." American Journal of Roentgenology 183.1 (2004): 175-181.

Donoho, David L. et al. "The optimal hard threshold for singular values is 4." arXiv preprint arXiv: 1305.5870 (2013).

Giannakis, Dimitrios. "Data-driven spectral decomposition and forecasting of ergodic dynamical systems." Applied and Computational Harmonic Analysis 47.2 (2019): 338-396.

Giannakis, Dimitrios, et al. "Nonlinear Laplacian spectral analysis for time series with intermittency and low-frequency variability." Proceedings of the National Academy of Sciences 109.7 (2012): 2222-2227.

Grebogi, Celso, et al. "Critical exponents for crisis-induced intermittency." Physical Review A 36.11 (1987): 5365.

Guckenheimer, John, et al. Nonlinear oscillations, dynamical systems, and bifurcations of vector fields. vol. 42. Springer Science & Business Media, 2013.

Hossen, Abdulnasir. "A new simple efficient classification technique for severity of sleep apnea with mathematical model and interpretation." Technology and Health Care 27.4 (2019): 389-406.

Hramov, Alexander E., Alexey A. Koronovskii, and Maria K. Kurovskaya. "Intermittent behavior near the synchronization threshold in system with fluctuating control parameter." Europhysics Letters 105.5 (2014): 50003.

Huynh, Phat K., et al. "Probabilistic domain-knowledge modeling of disorder pathogenesis for dynamics forecasting of acute onset." Artificial intelligence in medicine 115 (2021): 102056.

Juang, Jer-Nan, and Richard S. Pappa. "An eigensystem realization algorithm for modal parameter identification and model reduction." Journal of guidance, control, and dynamics 8.5 (1985): 620-627.

Kantz, Holger, and Thomas Schreiber. Nonlinear time series analysis. Cambridge university press, 2003.

Koopman, Bernard O. "Hamiltonian systems and transformation in Hilbert space." Proceedings of the National Academy of Sciences 17.5 (1931): 315-318.

Kunisaki, Ken M., et al. "Provider types and outcomes in obstructive sleep apnea case finding and treatment: a systematic review." Annals of internal medicine 168.3 (2018): 195-202.

Le, Trung Q., and Satish TS Bukkapatnam. "Nonlinear dynamics forecasting of obstructive sleep apnea onsets." PloS one 11.11 (2016): e0164406.

Le, Trung Q., et al. "Wireless wearable multisensory suite and real-time prediction of obstructive sleep apnea episodes." IEEE journal of translational engineering in health and medicine 1 (2013): 2700109-2700109.

Lilly, Jonathan M. "Element analysis: A wavelet-based method for analysing time-localized events in noisy time series." Proceedings of the Royal Society A: Mathematical, Physical and Engineering Sciences 473.2200 (2017): 20160776.

Majda, Andrew J., and John Harlim. "Physics constrained nonlinear regression models for time series." Nonlinearity 26.1 (2012): 201.

Majda, Andrew J., and Yoonsang Lee. "Conceptual dynamical models for turbulence." Proceedings of the National Academy of Sciences 111.18 (2014): 6548-6553.

Mendez, Martin O., et al. "Sleep apnea screening by autoregressive models from a single ECG lead." IEEE transactions on biomedical engineering 56.12 (2009): 2838-2850.

Mezić, Igor. "Spectral properties of dynamical systems, model reduction and decompositions." Nonlinear Dynamics 41 (2005): 309-325.

Nussbaumer, Henri J., and Henri J. Nussbaumer. The fast Fourier transform. Springer Berlin Heidelberg, 1982.

Park, Choongseok, Robert M. Worth, and Leonid L. Rubchinsky. "Fine temporal structure of beta oscillations synchronization in subthalamic nucleus in Parkinson's disease." Journal of neurophysiology 103.5 (2010): 2707-2716.

Pecchia, Leandro, et al. "Are ultra-short heart rate variability features good surrogates of short-term ones? State-of-the- art review and recommendations." Healthcare technology letters 5.3 (2018): 94-100.

Penzel, Thomas, et al. "The apnea-ECG database." Computers in Cardiology 2000. vol. 27 (Cat. 00CH37163). IEEE, 2000.

Rozenbaum, Efim B., Sriram Ganeshan, and Victor Galitski. "Lyapunov exponent and out-of-time-ordered correlator's growth rate in a chaotic system." Physical review letters 118.8 (2017): 086801.

Shelhamer, Mark. Nonlinear dynamics in physiology: a state-space approach. World Scientific, 2007.

Sugihara, George, et al. "Detecting causality in complex ecosystems." science 338.6106 (2012): 496-500.

Takens, Floris. "Dynamical systems and turbulence." Warwick, 1980 (1981): 366-381.

Tu, Jonathan H. Dynamic mode decomposition: Theory and applications. Diss. Princeton University, 2013.

Urtnasan, Erdenebayar, et al. "Automated detection of obstructive sleep apnea events from a single-lead electrocardiogram using a convolutional neural network." Journal of medical systems 42 (2018): 1-8.

Vautard, Robert, Pascal Yiou, and Michael Ghil. "Singular-spectrum analysis: A toolkit for short, noisy chaotic signals." Physica D: Nonlinear Phenomena 58. 1-4 (1992): 95-126.

Vollmer, Marcus. "HRVTool—an open-source matlab toolbox for analyzing heart rate variability." 2019 Computing in Cardiology (CinC). IEEE, 2019.

Wang, Shou-Yan, et al. "Time-frequency analysis of transient neuromuscular events: dynamic changes in activity of the subthalamic nucleus and forearm muscles related to the intermittent resting tremor." Journal of neuroscience methods 145.1-2 (2005): 151-158.

Williams, Matthew O., Ioannis G. Kevrekidis, and Clarence W. Rowley. "A data-driven approximation of the koopman operator: Extending dynamic mode decomposition." Journal of Nonlinear Science 25 (2015): 1307-1346.

Wu, Xiaodan, et al. "Extracting deep features from short ECG signals for early atrial fibrillation detection." Artificial Intelligence in Medicine 109 (2020): 101896.

Ye, Hao, et al. "Equation-free mechanistic ecosystem forecasting using empirical dynamic modeling." Proceedings of the National Academy of Sciences 112.13 (2015): E1569-E1576.

Zaslavsky, George M. Hamiltonian chaos and fractional dynamics. Oxford University Press, USA, 2005.

* cited by examiner

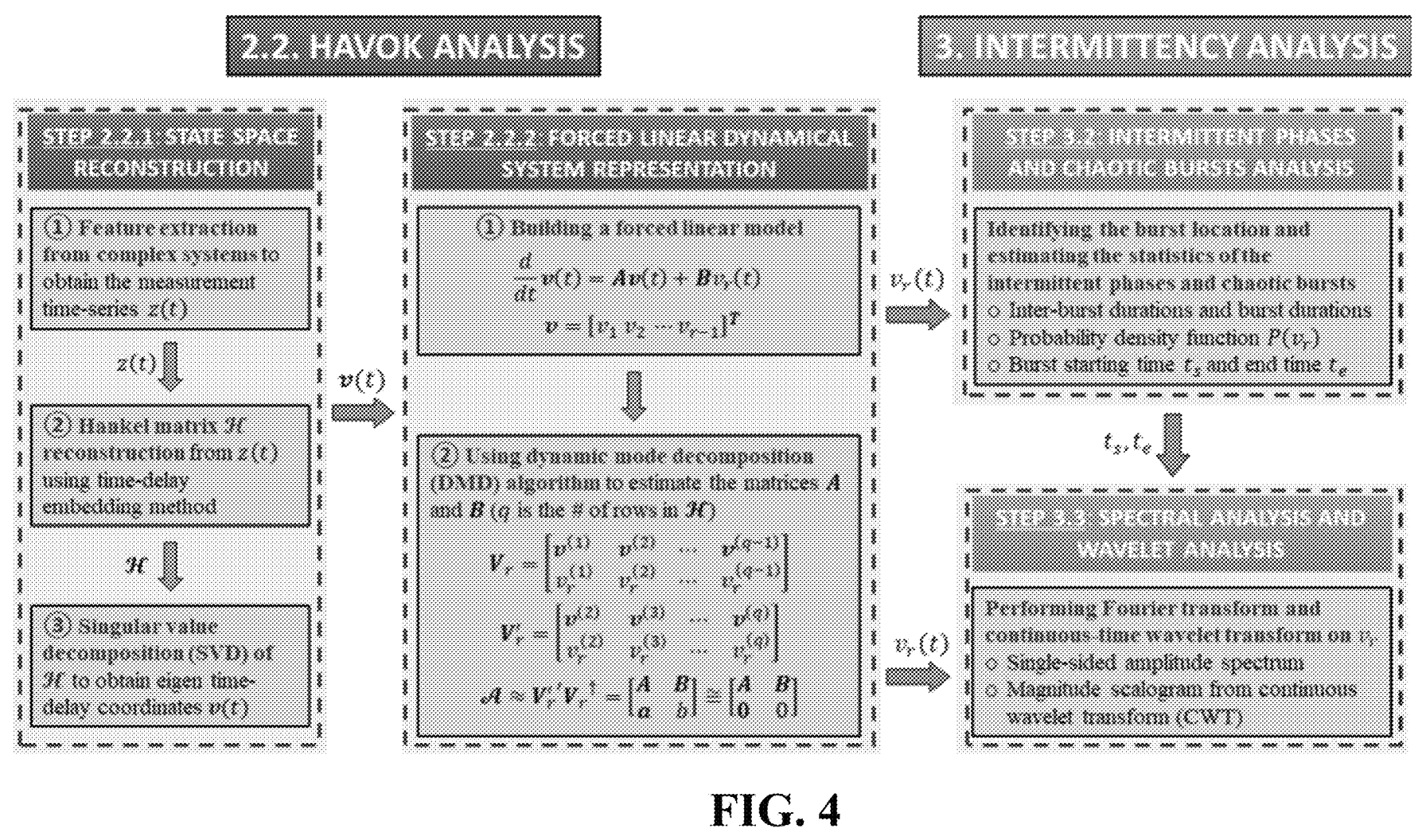

3. INTERMITTENCY ANALYSIS

STEP 2.3.1 INTERMITTENT PHASES AND DURATION CHARACTERIZATION

Identifying the burst location and estimating the statistics of the intermittent phases and chaotic bursts
- Inter-burst durations and burst durations
- Probability density function $P(\tau_q)$
- Burst starting time $t_s$ and end time $t_e$ $t_s, t_e$

STEP 2.3.2 SPECTRAL ANALYSIS

Performing Fourier transform and continuous time wavelet transform on $v_r$
- Single-sided amplitude spectrum
- Magnitude scalogram from continuous wavelet transform (CWT)

$v_r(t)$     $v_r(t)$

2.2 HAVOK ANALYSIS

STEP 2.2.2 FORCED LINEAR DYNAMICAL SYSTEM REPRESENTATION

① Building a forced linear model $$\frac{d}{dt}x(t) = Ax(t) + Bv_r(t)$$

$$v = [v_1, v_2, \cdots v_{r-1}]^T$$

② Using dynamic mode decomposition (DMD) algorithm to estimate the matrices $A$ and $B$ ($q$ is the # of rows in $\mathcal{H}$)

$$V_1 = \begin{bmatrix} v^{(1)} & v^{(2)} & \cdots \\ \vdots & \vdots & \ddots \end{bmatrix} \quad V_2 = \begin{bmatrix} v^{(2)} & v^{(3)} & \cdots \\ \vdots & \vdots & \ddots \end{bmatrix}$$

$$A \approx V_2 V_1^\dagger \quad [A \; B] = \begin{bmatrix} A & B \\ a & b \end{bmatrix} = \begin{bmatrix} A & B \\ 0 & 0 \end{bmatrix}$$

$v_r(t)$

STEP 2.2.1 TIME-SPACE RECONSTRUCTION

① Feature extraction from complex systems to obtain the measurement time-series $z(t)$ $z(t)$ ② Hankel matrix $\mathcal{H}$ reconstruction from $z(t)$ using time-delay embedding method $\mathcal{H}$ ③ Singular value decomposition (SVD) of $\mathcal{H}$ to obtain eigen time-delay coordinates $v(t)$

FIG. 4

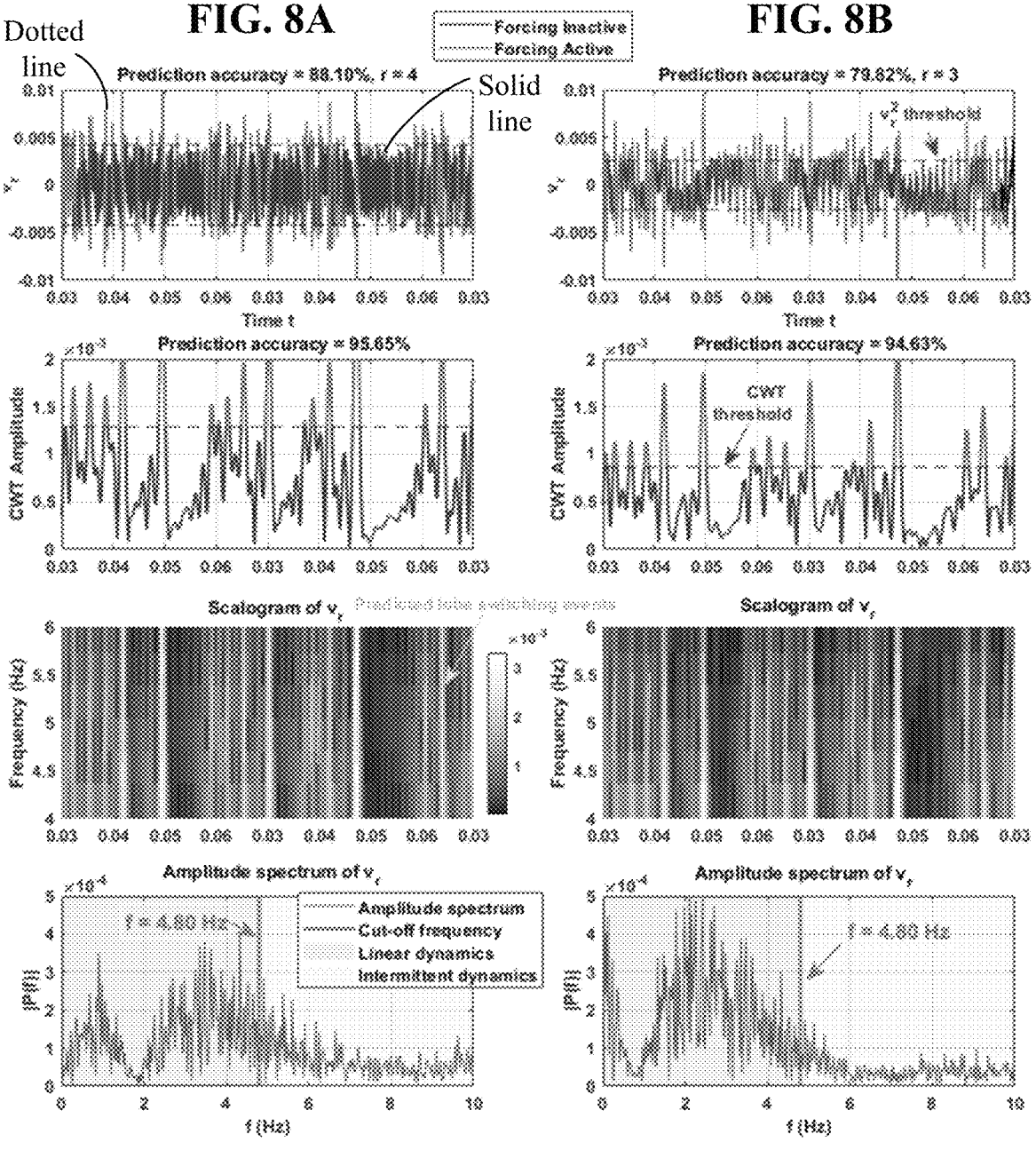

FIG. 10A                    FIG. 10B
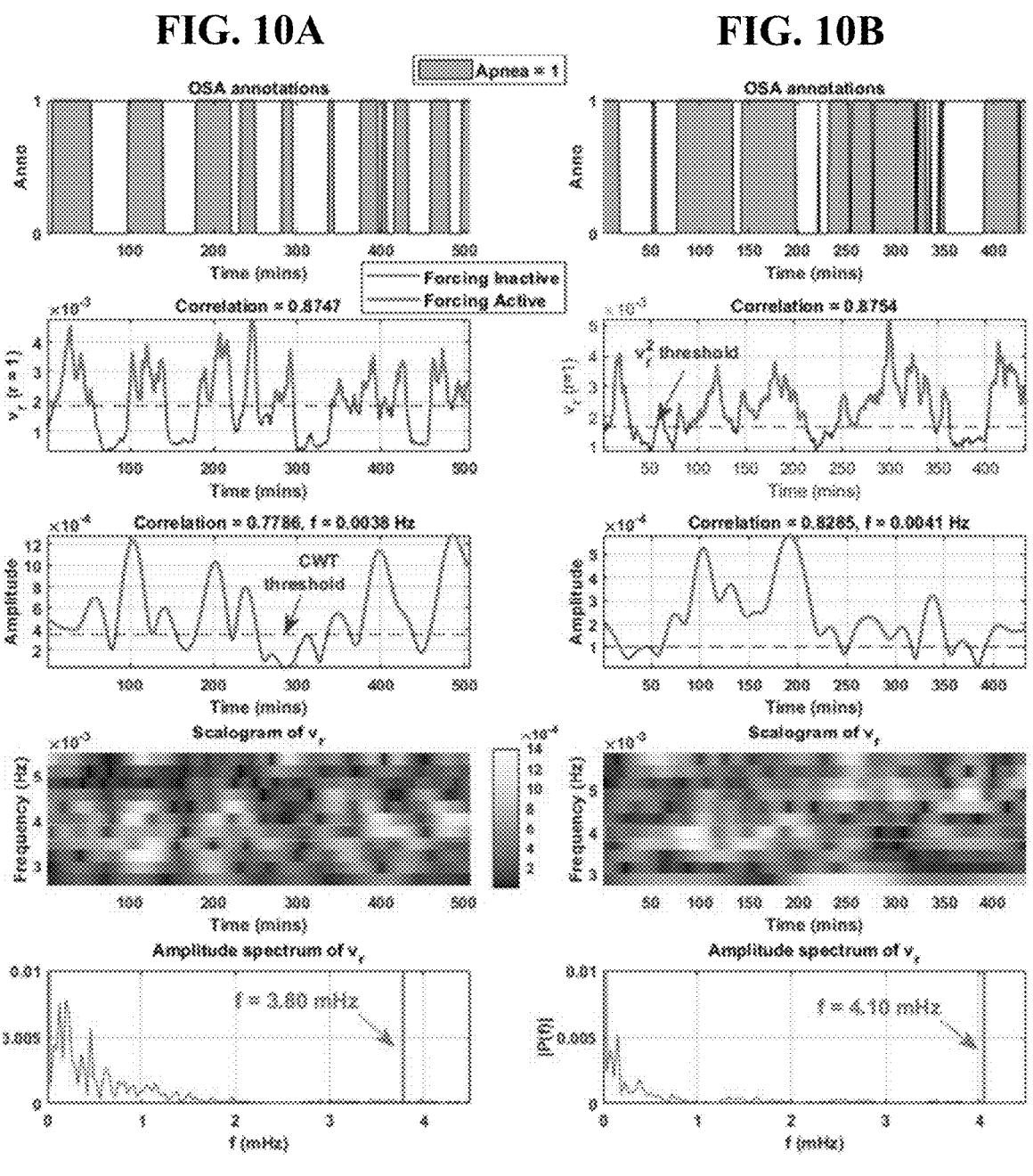

"Fast" VDP system

"Slow" VDP system

Initial point    RBFS samples    RL-based samples

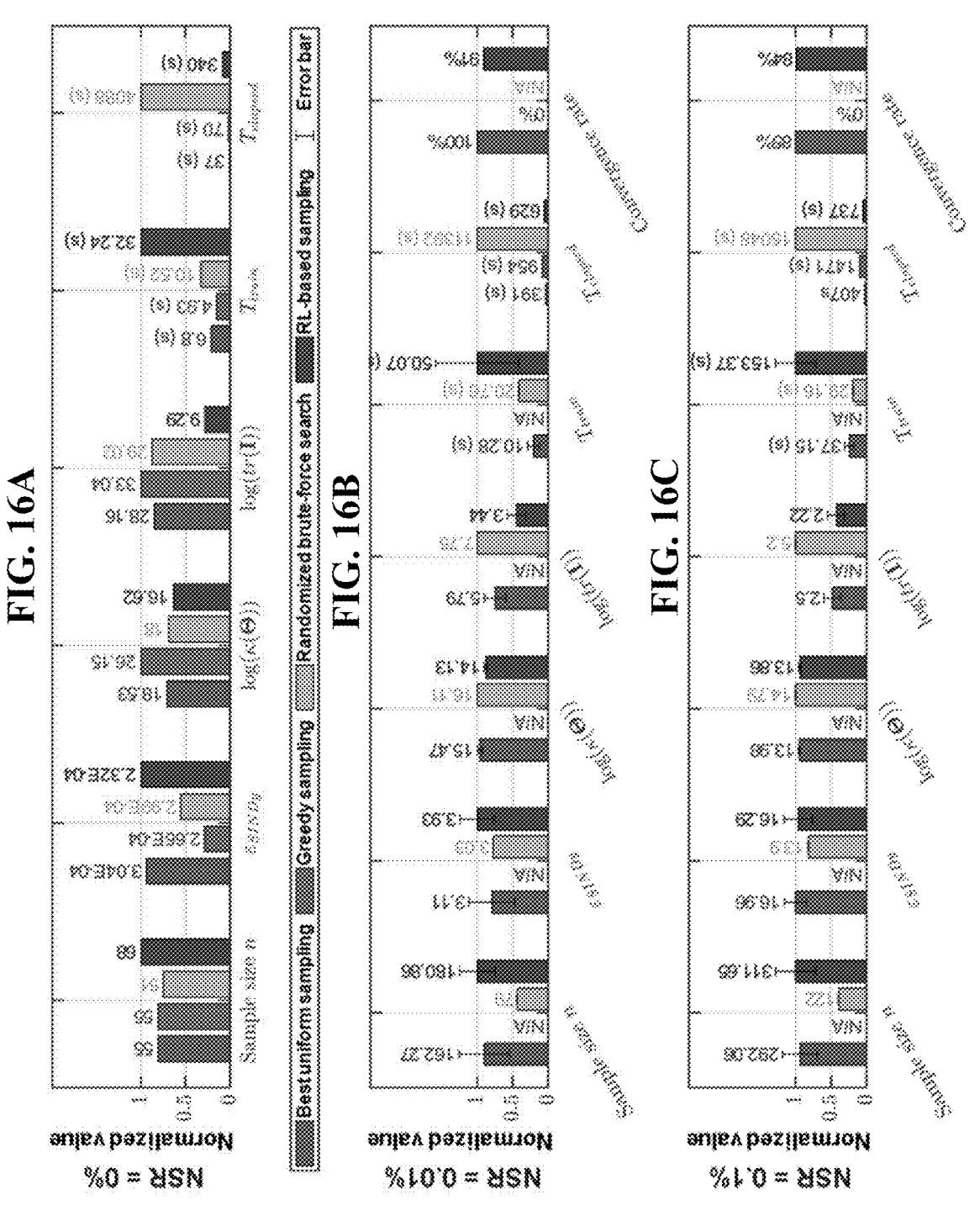

"Fast" VDP system     "Slow" VDP system

* Initial point    ∘ RBFS samples    × RL-based samples

1

NOISE-ROBUST SLEEP APNEA DIAGNOSTIC SYSTEM AND RELATED METHOD

CROSS-REFERENCE TO RELATED APPLICATION(S)

This application is based on, claims priority to, and incorporates herein by reference in their entirety U.S. Provisional Application Ser. No. 63/488,021, filed Mar. 2, 2023.

STATEMENT REGARDING FEDERALLY SPONSORED RESEARCH

This invention was made with government support under Award numbers U54GM128729 by the National Institute of General Medical Sciences of the National Institutes of Health and 2119691 by the National Science Foundation. The government has certain rights in the invention.

BACKGROUND

Modeling complex systems dynamics, which exhibit non-linearity, chaos, intermittency, transience, and uncertainty has become challenges in engineering and science. Among these behaviors, intermittency is one of common phenomena observed in many complex processes including pathophysiological processes. Intermittent dynamics have been observed in neuromuscular events in tremor, beta-oscillation synchronization events in Parkinson's disease, and obstruction of the posterior nasopharynx in obstructive sleep apnea. Although intermittency has been widely observed, the modeling and analysis of such behaviors have been not well-investigated in complex nonlinear systems with high-dimensional and nonlinear coupled dynamic physiological systems. As the demand for treating physiological obstruction (e.g., obstructive sleep apnea) continues to increase, research and development continue to advance obstructive sleep apnea detection and prediction technologies.

SUMMARY

The following presents a simplified summary of one or more aspects of the present disclosure, to provide a basic understanding of such aspects. This summary is not an extensive overview of all contemplated features of the disclosure and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

In some aspects of the present disclosure, methods, systems, and apparatus for obstructive sleep apnea diagnosis are disclosed. These methods, systems, and apparatus for agricultural monitoring may include steps or components for: obtaining a white noise contaminated sensor signal for a patient: extracting a feature based on the white noise contaminated sensor signal: determining a matrix based on the feature: determining an intermittent forcing signal based on the matrix: determining an overcomplete representation of the intermittent forcing signal; and generating an obstructive sleep apnea indication based on the overcomplete representation and a threshold.

These and other aspects of the disclosure will become more fully understood upon a review of the drawings and the detailed description, which follows. Other aspects, features, and embodiments of the present disclosure will become apparent to those skilled in the art, upon reviewing the following description of specific, example embodiments of the present disclosure in conjunction with the accompanying figures. While features of the present disclosure may be discussed relative to certain embodiments and figures below, all embodiments of the present disclosure can include one or more of the advantageous features discussed herein. In other words, while one or more embodiments may be discussed as having certain advantageous features, one or more of such features may also be used in accordance with the various embodiments of the disclosure discussed herein. Similarly, while example embodiments may be discussed below as devices, systems, or methods embodiments it should be understood that such example embodiments can be implemented in various devices, systems, and methods.

BRIEF DESCRIPTION OF THE DRAWINGS

FIG. 4 is a block diagram of an example process for obstructive sleep apnea diagnosis according to some embodiments.

FIG. 7A shows a time series coded by intermittent forcing, FIG. 7B shows a Lobe switching prediction, FIG. 7C shows a wavelet coefficients amplitude, FIG. 7D shows a magnitude scalogram, and FIG. 7E shows a single-sided amplitude spectrum.

FIGS. 8A and 8B show Hankel Alternative View Of Koopman (HAVOK) analysis and intermittency analysis for the noisy Lorenz system at 2 different noise to signal ratio values (1% for FIG. 8A and 10% for FIG. 8B).

FIGS. 10A and 10B show HAVOK analysis and intermittency analysis for two different patients.

FIGS. 15A, 15C, and 15E depict the samples for the fast Van der Pol (VDP) system under noise to signal ratio (NSR) settings of 0%, 0.1%, and 1%, respectively while FIGS. 15B, 15D, and 15F depict the samples for the slow VDP system under NSR settings of 0%, 0.1%, and 1% respectively.

FIGS. 16A-16C shows comparative analysis of different sampling strategies with a noise-free scenario in FIG. 16A, low noise conditions in FIG. 16B, and moderate noise conditions in FIG. 16C.

FIGS. 17A, 17C, and 157E depict the samples for the fast Van der Pol (VDP) system under noise to signal ratio (NSR) settings of 0%, 0.1%, and 1%, respectively while FIGS. 17B, 17D, and 17F depict the samples for the slow VDP system under NSR settings of 0%, 0.1%, and 1% respectively.

DETAILED DESCRIPTION

The detailed description set forth below in connection with the appended drawings is intended as a description of various configurations and is not intended to represent the only configurations in which the subject matter described herein may be practiced. The detailed description includes specific details to provide a thorough understanding of various embodiments of the present disclosure. However, it will be apparent to those skilled in the art that the various features, concepts and embodiments described herein may be implemented and practiced without these specific details. In some instances, well-known structures and components are shown in block diagram form to avoid obscuring such concepts.

Figure 1:
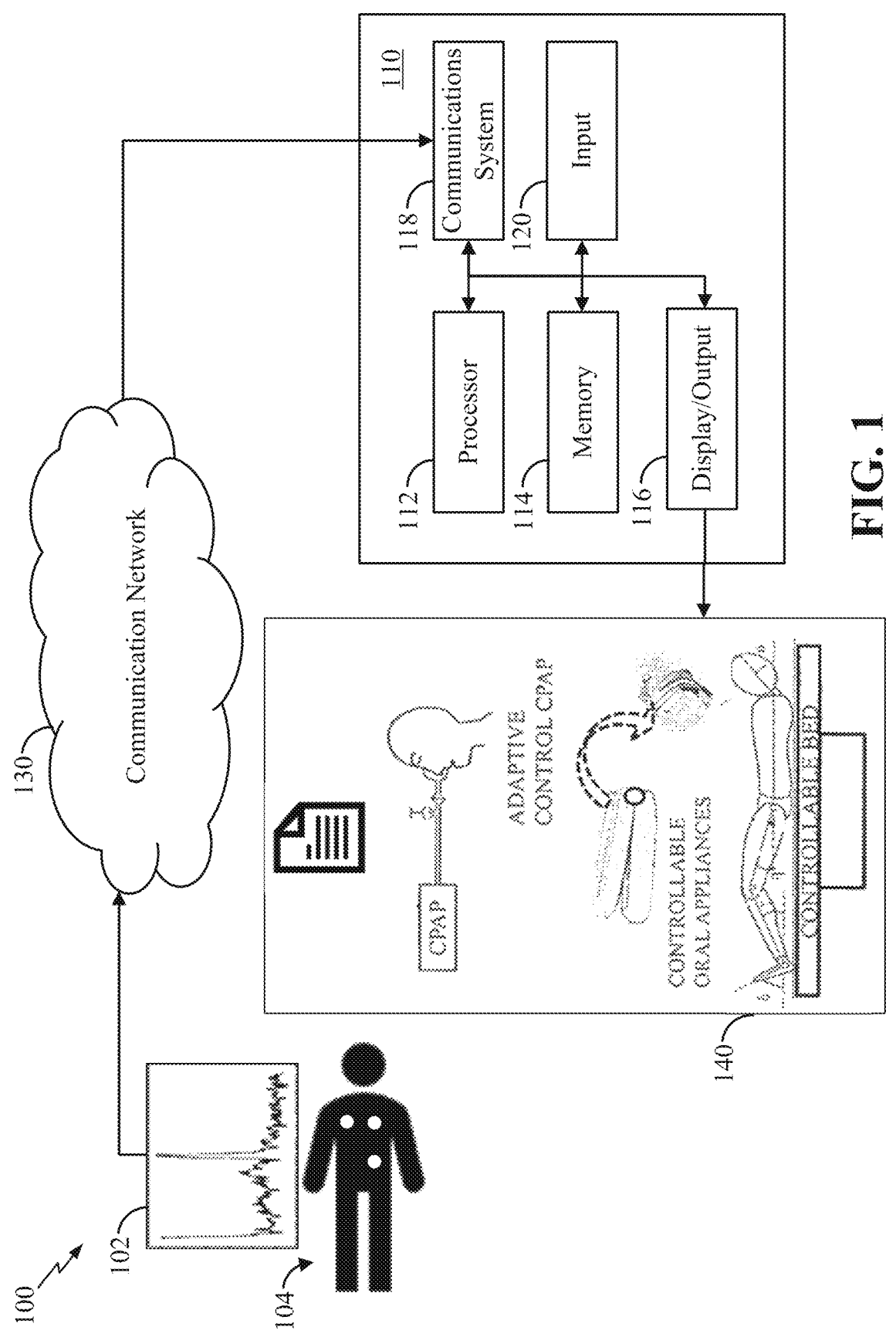
FIG. 1 is a block diagram conceptually illustrating a system for obstructive sleep apnea diagnosis according to some embodiments.

Intermittency is defined as the erratic alternations between periodic (i.e., regular and laminar) dynamics and chaotic (i.e., irregular and turbulent), commonly characterized by short bursts in the signal. Intermittency also exists in the other form of chaotic dynamics called crisis-induced intermittency. However, the study of intermittent dynamics is considerably challenging. Bifurcation analysis from the governing equations is the classical approach to studying the system behaviors as the parameters are perturbed. However, there are increasing numbers of complex systems for which abundant measurement data exists from sensors but the underlying parameterized governing equations are unknown. Hence, an interpretable data-driven method that accurately models the intermittent dynamics of high-dimensional complex systems with unknown governing equations is needed. In the disclosed process, obstructive sleep apnea having the intermittent dynamics is analyzed using a data-driven model. DETAIL AND BENEFIT
Example Obstructive Sleep Apnea Diagnostic System FIG. 1 shows a block diagram illustrating a system for obstructive sleep apnea diagnosis according to some embodiments. In some examples, a computing device 110 can obtain or receive a sensor signal 102 for a patient and process the sensor signal 102 to generate an obstructive sleep apnea indication 140.

The sensor signal 102 can include a raw sensor signal or a white-noise contaminated sensor signal. In some examples, the sensor signal 102 can include an electrocardiogram (ECG or EKG) signal produced by an electrocardiogram sensor. In some examples, the ECG sensor measures the electrical activity of the heart through repeated cardiac cycles. In some examples, the sensor signal 102 may be an electrogram of the heart which is a graph of voltage versus time of the electrical activity of the heart using electrodes placed on suitable places on the body of the patient 104. In further examples, the sensor signal 102 can be an white noise contaminated sensor signal where white noise is added to the raw sensor signal. In other examples, the sensor signal can be produced by any other suitable sensor (e.g., heart sound sensor, vibrator, smart wrist band, smart ankle band, an accelerometer, a gyroscope, an inertial measurement unit (IMU) device, any other suitable sensors). The computing device 110 can receive the sensor signal 102, which is stored in a database, via communication network 130 and communications system 118 of computing device 110. For example, the sensor signal 102 can be a signal from a wireless signal acquisition board on the patient's body 104, which acquire signals from ECG electrodes, a heart sound sensor, a vibrator, and/or any other suitable sensor.

The computing device 110 can include a processor 112, a memory 114, a display 116, a communications system 118, and/or an input 120 to process the sensor signal 102 to produce the obstructive sleep apnea indication. In some embodiments, the processor 112 can be any suitable hardware processor or combination of processors, such as a central processing unit (CPU), a graphics processing unit (GPU), an application specific integrated circuit (ASIC), a field-programmable gate array (FPGA), a digital signal processor (DSP), a microcontroller (MCU), etc.

The memory 114 can include any suitable storage device or devices that can be used to store suitable data (e.g., sensor signal, obstructive sleep apnea indication, etc.) and instructions that can be used, for example, by the processor 112 to obtain a white noise contaminated sensor signal for a patient, extract a feature based on the white noise contaminated sensor signal, determine a matrix based on the feature, determine an intermittent forcing signal based on the matrix, determine an overcomplete representation of the intermittent forcing signal, generate an obstructive sleep apnea indication based on the overcomplete representation and a threshold, receive a sensor signal, add white noise in the sensor signal for the white noise contaminated sensor signal, determine a level of the white noise to make the intermittent forcing signal a Gaussian distribution, determine a burst duration and an inter-burst duration between two adjacent burst durations, determine an obstructive sleep apnea characteristic for the patient based on the burst duration and the inter-burst duration, determine multi-scale system dynamics, and adaptively sample the sensor signal based on the multi-scale system dynamics for the white noise contaminated sensor signal. The memory 114 can include any suitable volatile memory, non-volatile memory, storage, or any suitable combination thereof. For example, memory 114 can include random access memory (RAM), read-only memory (ROM), electronically-erasable programmable read-only memory (EEPROM), one or more flash drives, one or more hard disks, one or more solid state drives, one or more optical drives, etc. In some embodiments, the processor 112 can execute at least a portion of process 200 described below in connection with FIG. 2.

The communications system 118 can include any suitable hardware, firmware, and/or software for communicating information over communication network 130 and/or any other suitable communication networks. For example, communications system 118 can include one or more transceivers, one or more communication chips and/or chip sets, etc.

In a more particular example, communications system 118 can include hardware, firmware and/or software that can be used to establish a Wi-Fi connection, a Bluetooth connection, a cellular connection, an Ethernet connection, etc.

In some examples, the computing device 110 can receive or transmit information (e.g., the sensor signal 102, the obstructive sleep apnea indication 140, etc.) and/or any other suitable system over a communication network 130. In some examples, the communication network 130 can be any suitable communication network or combination of communication networks. For example, the communication network 130 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, NR, etc.), a wired network, etc. In some embodiments, communication network 130 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

The display 116 can include any suitable display devices, such as a computer monitor, a touchscreen, a television, an infotainment screen, etc. to display the report, the obstructive sleep apnea activity indication 140, or any suitable result of obstructive sleep apnea detection or prediction. The input 120 can include any suitable input devices (e.g., a keyboard, a mouse, a touchscreen, a microphone, etc.) and/or a sensor that can produce the sensor signal.

In some examples, the computing device 110 can output a conductive thread (e.g., to a controllable oral appliance, a controllable bed to adjust a body position of the patient 104, an adaptive control CPAP (Continuous Positive Airway Pressure). Thus, based on the obstructive sleep apnea indication 140, the computing device 110 can provide a control of any other suitable apparatus to correct the obstructive sleep apnea or hypopnea.

Example Obstructive Sleep Apnea Diagnosis Process

Figure 2:
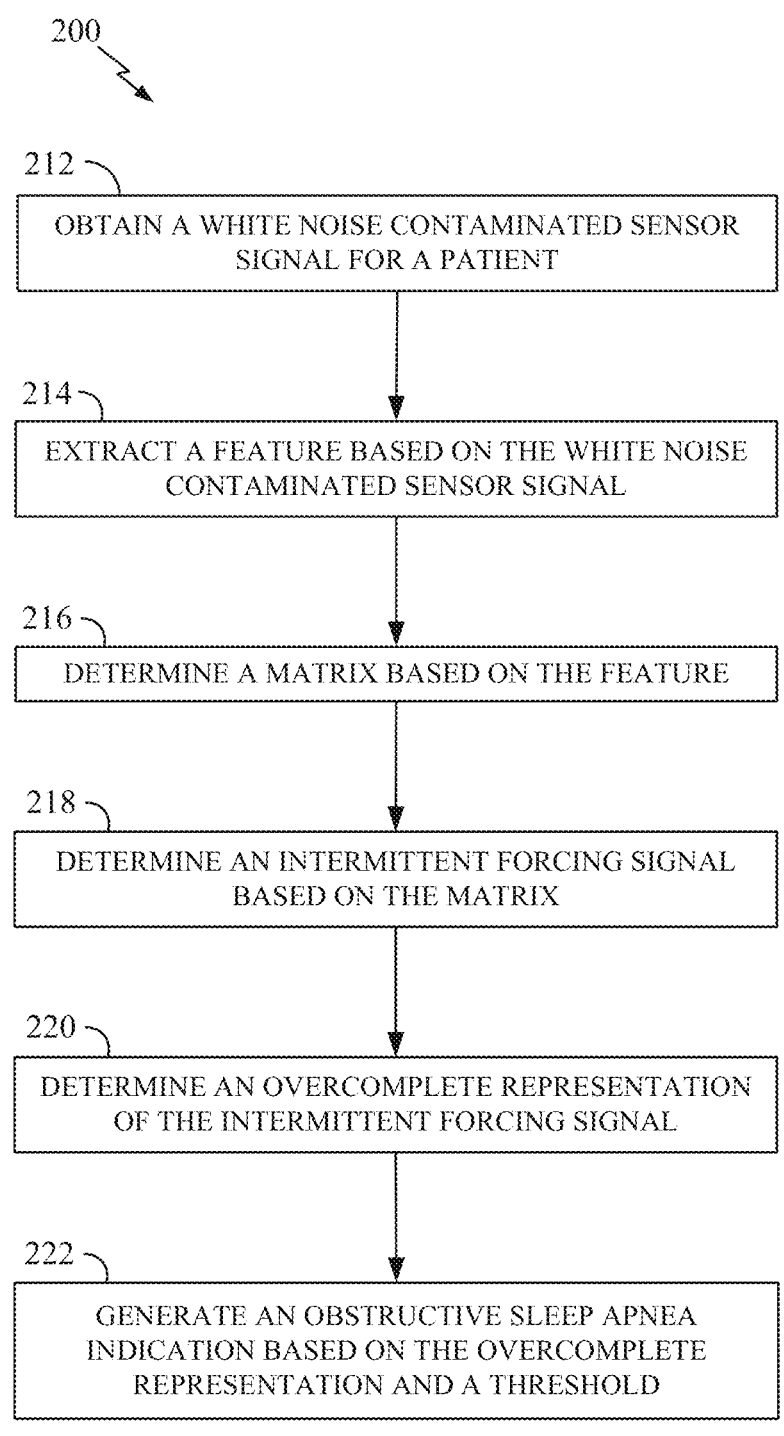
FIG. 2 is a flow diagram illustrating an example process for obstructive sleep apnea diagnosis according to some embodiments.

FIG. 2 is a flow diagram illustrating an example process 200 for obstructive sleep apnea diagnosis in accordance with some aspects of the present disclosure. As described below; a particular implementation can omit some or all illustrated features/steps, may be implemented in some embodiments in a different order, and may not require some illustrated features to implement all embodiments. In some examples, an apparatus (e.g., computing device 110, processor 112 with memory 114, etc.) in connection with FIG. 1 can be used to perform example process 200. However, it should be appreciated that any suitable apparatus or means for carrying out the operations or features described below may perform process 200.

At step 212, the process 200 can obtain a white noise contaminated sensor signal for a patient. The white noise contaminated sensor signal can include an electrocardiogram (ECG) signal. In some examples, the process can record the ECG signal for the patient from 7 hours to 10 hours to diagnose the obstructive sleep apnea. In further examples, the white noise contaminated sensor signal can include any other sensor signal detecting any intermittency. The white noise can be artificially induced white noise or natural noise in the raw sensor signal. For example, to obtain the white noise contaminated sensor signal, the process 200 can receive a sensor signal (e.g., raw ECG sensor signal) and add white noise in the sensor signal for the white noise contaminated sensor signal. In some examples, the process 200 can further determine a level of the white noise to make an intermittent forcing signal (e.g., determined at step 218 of the process 200 below) a Gaussian distribution. For example, the process can determine the level of the white noise to be 0.1%, 1%, 10%, 50%, or any suitable level of a noise-to-signal ratio (NSR). In further examples, the white noise can be naturally included noise in the raw sensor signal. In such examples, the white noise contaminated sensor signal can be raw sensor signal with minimally performing a pre-processing step to reduce noise. Even with the minimal pre-processing, the process 200 can provide a reliable and accurate diagnosis and prediction of obstructive sleep apnea. In addition, due to the noise-robust process 200, the process 200 can reduce the time to provide or provide in near real-time the obstructive sleep diagnosis. Alternatively or additionally, the process 200 can perform a signal processing on the raw sensor signal (e.g., the ECG signal). For example, a bandpass filter (e.g., a 5th order Butterworth 0.5-30 Hz bandpass filter) can be applied to the signal to eliminate noise and baseline wandering. However, any other suitable preprocessing can be performed to facilitate the analysis of the intermittency of the sensor signal. In some examples, the addition of white noise, which can be either artificially induced or naturally present in the raw sensor signal, helps in replicating real-world scenarios where sensor data is often contaminated with various kinds of noise. This approach enhances the robustness and reliability of the diagnosis and prediction process for obstructive sleep apnea, as it prepares the system to handle real-world, noisy data effectively.

In other examples, the process 200 can receive the white noise contaminated sensor signal over the communication network 130. For example, the process 200 can receive the white noise contaminated sensor signal from a database (e.g., the Apnea-ECG Database) over the communication network 130. Further, the process 200 can receive the white noise contaminated sensor signal from any other suitable source (e.g., a personal device of the patient, a computing device for a physician, a sensor having the computing and information transmission capability, etc.).

At step 214, the process 200 can extract a feature based on the white noise contaminated sensor signal. For example, the feature can include a heart rate variability (VAR) feature to quantify time intervals between adjacent heartbeats. Thus, the feature can quantify the fluctuation in the time intervals between adjacent heartbeats, which arise from the neuro-cardiac functions, the heart-brain interactions, and dynamic non-linear autonomic nervous system (ANS) processes. For example, the feature can include, but is not limited to, approximate entropy (ApEn), sample entropy (SampEn), detrended fluctuation analysis (DFA), a Poincaré plot standard deviation perpendicular the line of identity (SD1), a Poincaré plot standard deviation along the line of identity (SD2), an area of the ellipse which represents total heart rate variability (S), a correlation dimension ($D_2$), a triangular index (TRI), etc. In some examples, the feature can be more than one feature. For example, the process can extract a set of multiple features (e.g., 18 features or any other suitable features). In such examples, the process can select the most appropriate feature among the multiple features for the subsequent step (e.g., the step 216 of the process 200). For example, the most appropriate feature can be predetermined based on the strongest correlation between the active forcing and hypopnea-apnea events. The most appropriate feature can be predetermined for all patients or determined based on each patient based on the medical record or any other suitable information of the respective patient. For example, the most appropriate feature for some patients can be DFA while the most appropriate feature for other patients can be TRI. In some examples, the most suitable HRV feature can be the one the shows the strongest correlation with the active forcing and hypopnea or apnea events. This means identifying which HRV metrics most accurately reflect the fluctuations in heart rate that are associated with these respiratory events. In further examples, the selection can be tailored based on individual patient data. This implies that the most appropriate HRV feature might vary from one patient to another, depending on their medical history or specific characteristics of their heart rate patterns. For some patients, a feature like DFA (Detrended Fluctuation Analysis) might be more relevant, while for others, TRI (Triangular Index) could be more appropriate. Clustering algorithm is be used to determine the patient group. The feature can include quantified spectral energy and nonlinear patterns of the white noise contaminated sensor signal. In some examples, the sliding window length can be selected to be a predetermined time period (e.g., one minute or any other suitable time period).

At step 216, the process 200 can determine a matrix based on the feature. For example, the matrix can include a Hankel matrix ($\mathcal{H}$) reconstructed from the extracted feature (z(t)). The matrix can include a window length of the feature (i.e., p) and a number of points in a trajectory of the feature (i.e., q). Thus, the matrix ($\mathcal{H}$) can have the size of q×p from the extracted feature, where q=N−p+1, N is the length of the feature time series, and p is the window length. In some examples, the q value can be chosen such that the maximum periodicity of the underlying dynamics can be captured.

For example, the extracted feature can be denoted as $$\{z(t_i)\}_{i=1}^T,$$

where $t_i$ is a sampling time points. Next, the eigen-time-delay coordinates can be computed from $$\{z(t_i)\}_{i=1}^T$$

by taking the singular value decomposition (SVD) of the Hankel matrix $\mathcal{H}$ or the trajectory matrix $\mathcal{D}$ in singular spectrum analysis (SSA) as:

$$\mathcal{H} = \begin{bmatrix} z(t_1) & z(t_2) & \dots & z(t_p) \\ z(t_2) & z(t_3) & \dots & z(t_{p+1}) \\ \vdots & \vdots & \ddots & \vdots \\ z(t_q) & z(t_{q+1}) & \dots & z(t_T) \end{bmatrix} = U\Sigma V^*,$$

where q is the number of points in the trajectory and p is the window length. The window length, p, can determine the extent to which a refined decomposition is obtained into basic components and therefore improve the separability of the dynamics. In other words, the window length p can define the longest dynamics periodicity captured by the Hankel matrix in the Hankel Alternative View Of Koopman (HAVOK) model. The columns U and V can be arranged hierarchically corresponding to the descending order of singular values in Σ. In addition, $\mathcal{H}$ often admits a low-rank approximation by the truncation of the first r columns of U and V. The low-rank approximation to $\mathcal{H}$ can give rise to a measurement subspace that is approximately invariant to $\mathcal{K}$. Consequently, the matrix can be rewritten with the Koopman operator $\mathcal{K}$:

$$\mathcal{H} = \begin{bmatrix} z(t_1) & \mathcal{K}z(t_1) & \dots & \mathcal{K}^{p-1}z(t_1) \\ \mathcal{K}z(t_1) & \mathcal{K}^2z(t_1) & \dots & \mathcal{K}^pz(t_1) \\ \vdots & \vdots & \ddots & \vdots \\ \mathcal{K}^{q-1}z(t_1) & \mathcal{K}^qz(t_1) & \dots & \mathcal{K}^{T-1}z(t_1) \end{bmatrix}.$$

The columns and rows of $\mathcal{H}$ are well-approximated by the first r truncated columns and rows of U and V respectively, which are called an eigen time series, providing a Koopman-invariant measurement system.

At step 218, the process 200 can determine an intermittent forcing signal based on the matrix. For example, the process 200 can determine the intermittent forcing signal (i.e., $v_r(t)$), which is in eigen time-delay coordinates, by decomposing the matrix. In some examples, the process 200 can determine a hard threshold (i.e., $$v_r^2$$

which can be applied to the intermittent forcing signal to determine an obstructive sleep apnea indication. This $$v_r^2$$

thresholding approach can be useful and effective when the sensor signal is without noise (i.e., 0% of NSR) or with minimal noise.

In some examples, the rows of V can be considered as a set of coordinates to construct a linear dynamical system. However, a linear model cannot fully capture multiple fixed points, periodic orbits, and the unpredictable chaos with a positive Lyapunov exponent. To overcome, a forced linear system has been proposed after applying the dynamic mode decomposition (DMD) algorithm to the delay coordinates and obtaining an excellent linear fit for the first r−1 variables but a bad fit for $v_r$. Particularly, the connection between the eigentime-delay coordinates and the Koopman operator, $\mathcal{K}$, shown above induce a linear regression model, in which a linear model is built on the first r−1 variables in V and consider $v_r$ as an intermittent forcing signal or term as follows:

$$\frac{d}{dt}v(t) = Av(t) + Bv_r(t) = \frac{d}{dt}\begin{bmatrix} v_1 \\ v_2 \\ \vdots \\ v_{r-1} \\ v_r \end{bmatrix} = \begin{bmatrix} A & B \\ 0 & 0 \end{bmatrix}\begin{bmatrix} v_1 \\ v_2 \\ \vdots \\ v_{r-1} \\ v_r \end{bmatrix},$$

$$\text{where } v = [v_1 \quad v_2 \quad \dots \quad v_{r-1}]^T$$

is a vector of the first r−1 eigen time-delay coordinates. In principle, the eigen time-delay variables can be separated into r−s high-energy modes for the linear model and s low-energy intermittent forcing modes if $v_r(t)$ may not sufficient to model the intermittent forcing. The partition of nonlinear dynamics into deterministic linear dynamics and chaotic dynamics was proposed. The truncated rank, r, can be estimated by the optimal hard threshold for singular values. The HAVOK model extends the dynamics splitting concept to fully chaotic systems, in which the Koopman operators have continuous spectra. The matrices A and B can be estimated as follows:

$$V_r = \begin{bmatrix} v^{(1)} & v^{(2)} & \dots & v^{(q-1)} \\ v_r^{(1)} & v_r^{(2)} & \dots & v_r^{(q-1)} \end{bmatrix}, V_r' = \begin{bmatrix} v^{(2)} & v^{(3)} & \dots & v^{(q)} \\ v_r^{(2)} & v_r^{(3)} & \dots & v_r^{(q)} \end{bmatrix},$$

$$\mathcal{A} \approx V_r'^T V_r^{\dagger} = \begin{bmatrix} A & B \\ a & b \end{bmatrix} \cong \begin{bmatrix} A & B \\ 0 & 0 \end{bmatrix}.$$

$$V_r'$$

is the 1-step time advanced eigen time-delay coordinates of $V_r$. These matrices, $V_r$ and $$V_r',$$

are related by a best-fit linear operator, $\mathcal{A}$, that minimizes the Frobenius norm error $$\|V_r' - \mathcal{A}V_r\|_F,$$

and $$V_r^{\dagger}$$

is the pseudo-inverse computed via the SVD of $V_r$. The estimates a and b are considered a bad fit for $v_r$ and approximate to zero. For complex systems of relatively large dimension, operator $\mathcal{A}$ is also large; therefore, the DMD method or more advanced methods (e.g., the sparse identification of nonlinear dynamical systems (SINDy) method can be applied to consider only the leading eigen-decomposition of $\mathcal{A}$.

In some examples, the process 200 can determine a burst duration and an inter-burst duration between two adjacent burst durations. For example, the two adjacent burst durations can include a first burst duration (e.g., which is a prior burst duration in time) and a second burst duration (e.g., which is a subsequent burst duration in time). Thus, the inter-burst duration can include a duration between an end time of the first burst duration and a starting time of the second burst duration. The process 200 can determine an obstructive sleep apnea characteristic for the patient based on the burst duration and the inter-burst duration. For example, a burst represents a period of abnormal respiratory activity or other physiological changes indicative of obstructive sleep apnea events. By calculating the start and end times of these bursts, the process can precisely identify when these abnormal events occur. The duration of these bursts and the time intervals between them (inter-burst duration) can provide insight into the severity and frequency of apnea events. Longer bursts or shorter inter-burst durations may indicate more severe apnea. In other examples, the burst-related time and duration can be separately calculated based on the CWT threshold. The burst-related times and durations determined by each method could differ based on their respective abnormal respiratory activity or other physiological changes they capture and sensitivity to signal variations.

HAVOK analysis can be applied to many nonlinear dynamical systems including analytical systems, stochastic magnetic field reversal, and real-world systems. The distribution of the intermittent forcing $v_r(t)$ in those examples was shown to be nearly symmetric with fat tails, i.e., the distributions are non-Gaussian. The distribution of the burst durations can be denoted as $T_b(k) \in (0, \infty)$, with $k=1, \dots, N_b$ as the burst index. First, a hard threshold for detecting the active forcing (i.e., intermittent bursts) is selected such that if $$v_r^2(t) \geq \psi \max\{v_r^2(t) \mid t \geq 0\}$$

then the forcing is active, where i is a tuning parameter. The $\psi$ parameter can be adjusted to achieve the best alignment with the intermittent behaviors of the system, e.g., lobe switching in the chaotic Lorenz system or disease onsets in pathophysiological processes. However, the statistics of the intermittent forcing are not adequate to characterize the mode switching of nonlinear dynamics and the fat-tailed non-Gaussian distribution originated from high-frequency bursts and rarely observed intermittent switching events. Therefore, additional statistics can be defined to better characterize the intermittent phases and chaotic bursts: the starting and ending time of the bursts as $t_s(k)$ and $t_e(k)$ and the burst duration as $T_b(k): =t_e(k)-t_s(k)$. Next, the inter-burst duration can be defined as $T_{ib}=t_s(k)-t_e(k-1)$ for $k=2, \dots, N_b$.

Figure 3A:
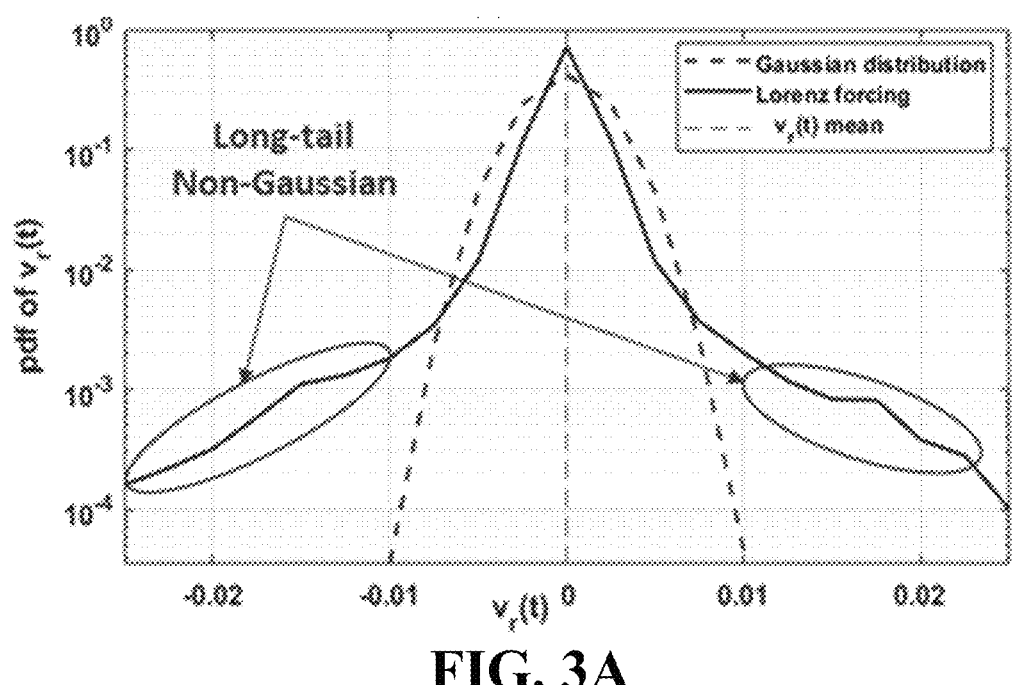
FIGS. 3A and 3B illustrate examples of statistics of intermittent phases and chaotic bursts, respectively according to some embodiments.
Figure 3B:
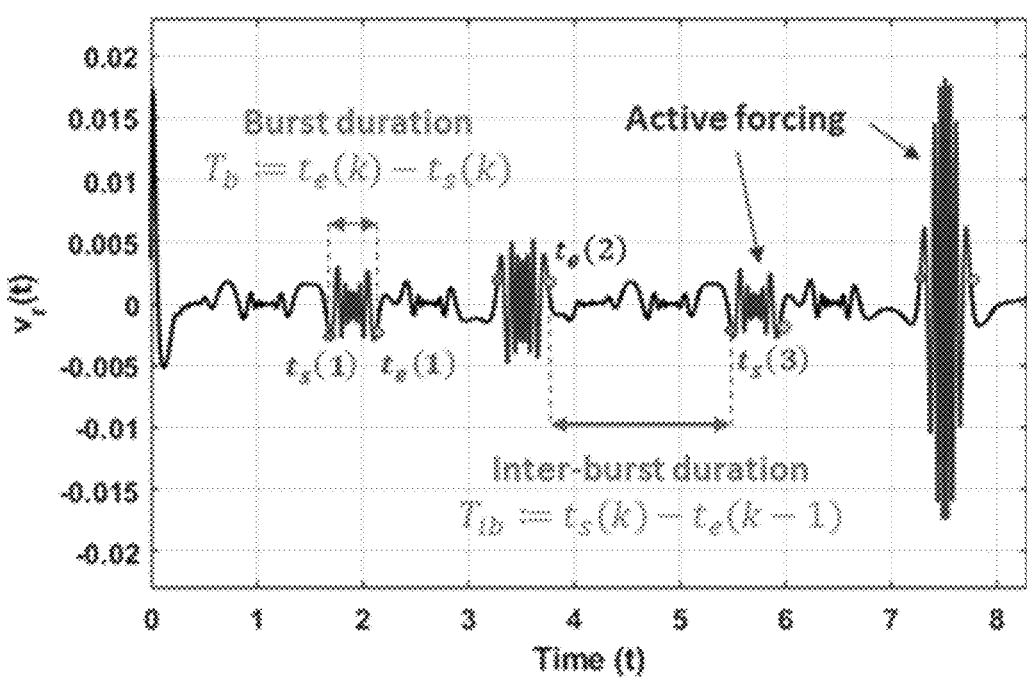

These statistics of intermittent phases and chaotic bursts are illustrated in FIGS. 3A and 3B, respectively. FIG. 3A shows the long-tail non-Gaussian distribution of the forcing term $v_r(t)$ for the Lorenz system. FIG. 3B illustrates the estimation of burst duration, $T_b$, and inter-burst duration, $T_{ib}$, in $v_r(t)$, where $t_s(k)$ and $t_e(k)$ are the starting time and ending time of the bursts. In some examples, the long-tail non-Gaussian distribution of the intermittent forcing signal can be shown when noise of the sensor signal is removed (i.e., NSR=0%). On the other hand, when the white noise is added for the NSR of the sensor signal to be 1%, 10%, or even 50%, the intermittent forcing signal may have an approximate Gaussian distribution.

At step 220, the process 200 can determine an overcomplete representation of the intermittent forcing signal. For example, the overcomplete representation is determined by applying a continuous wavelet transform to the intermittent forcing signal. In some examples, the continuous wavelet transform can be defined as:

$$X_w(a, b) = \frac{1}{|a|^{1/2}} \int_{-\infty}^{\infty} v_r(t) \bar{\psi}\left(\frac{t-b}{a}\right) dt,$$

where $X_w$ is the continuous wavelet transform (CWT), $\psi(t)$ is a continuous mother wavelet function and v is a complex conjugate, a is a scale, b is a translational value, and $v_r(t)$ is the intermittent forcing signal. An objective of the mother wavelet is to provide a function to generate the translated and scaled versions (called "daughter" wavelets) of the mother wavelet.

In some examples, for displaying the results of the CWT, the scalogram can be used to represent the absolute value of the CWT of a signal, which is plotted as a function of frequency and time. For the intermittency analysis, the scalogram representation is well suited to analyze the intermittent forcing $v_r(t)$ that occurs at different frequency scales. The scalogram computes the modulus of CWT coefficients (i.e., $|X_w|$), and time-localization can be obtained for short-duration, high-frequency burst events, and better separate them from low-frequency components and longer-duration events. To determine the active forcing, the threshold (e.g., a hard threshold) can be defined as $|X_w(a,b)| \geq \psi_{CWT} \max |X_w (a,b)|$, where $\psi_{CWT}$ is a tuning parameter. For example, a hard threshold is defined such that if $|X_w(a^*, b)| \geq \psi_{CWT} \max |X_w(a^*, b)|$ then the forcing is active, where $\psi_{CWT}$ and $a^*$ are the tuning parameter and the optimal scale to achieve the highest forcing prediction accuracy. In other examples, the threshold can be dynamic and adjusted for each patient based on the patient's data (e.g., body mass index (BMI), circumference of the neck, etc.).

At step 222, the process 200 can generate an obstructive sleep apnea indication based on the overcomplete representation and a threshold. For example, the obstructive sleep apnea indication can be a binary indication indicative of normal breathing or disordered breathing. In some examples, the binary indication can be determined based on a threshold number of apneas per hour. In further examples, the obstructive sleep apnea indication can further include a number of apneas or hypopneas per hour, an average duration of apneas or hypopneas, a severity level of apneas or hypopneas, or any other suitable indication.

In some examples, the process 200 can predict the obstructive sleep apnea. For example, although the obstructive sleep apnea indication may indicate normal breathing, the number of apneas or hypopneas per hour can be lower that the threshold to be disordered breathing but higher than a second threshold to be potential disordered breathing. In further examples, the CWT threshold can have two thresholds where a first CWT threshold is for the disorder breathing and a second CWT threshold is for a potential disordered breathing. In other examples, the process 200 can predict the obstructive sleep apnea by determining the obstructive sleep apnea indication several times for a certain period of time. For example, if the number of apneas or hypopneas per hour to be disordered breathing is five, the patient had two apneas per hour two months ago and had four apneas per hour a week ago. In such examples, the obstructive sleep apnea indication may indicate normal breathing. However, the process 200 can indicate that the patient is likely to experience disordered breathing within two months.

In some examples, the obstructive sleep apnea can be predicted by applying dual CWT thresholds, analyzing patterns with normal indications, or longitudinal monitoring. In some examples, the obstructive sleep apnea can be predicted by applying dual CWT thresholds. For example, the CWT (Continuous Wavelet Transform) method can be used with two thresholds. The first threshold identifies disordered breathing (indicative of OSA), while the second, possibly lower threshold, marks potential disordered breathing. This allows for the identification of patients who are on the borderline of developing OSA. Thus, the dual CWT thresholds can differentiate between sleep disorder and potential disorder. Also, for patients whose apnea/hypopnea frequency is above the lower threshold but below the higher threshold, there is an indication of potential disordered breathing. This can serve as an early warning, suggesting a need for closer monitoring or preventive measures.

In further examples, the obstructive sleep apnea can be predicted by analyzing patterns despite normal indications. For example, in cases where the obstructive sleep apnea indication may show normal breathing, but there is a consistent presence of apneas or hypopneas (though below the threshold for disordered breathing), the process can predict a likelihood of developing OSA. This is particularly relevant for patients whose apnea/hypopnea frequency is on an upward trajectory.

In other examples, the obstructive sleep apnea can be predicted by longitudinal monitoring. For example, predictions can be made by analyzing the obstructive sleep apnea indications repeatedly over a certain period. This longitudinal approach helps in understanding the progression of the condition and can indicate an increasing likelihood of developing OSA. Also, the process might also integrate various other physiological indicators (like heart rate variability, oxygen saturation levels, etc.) along with apnea/hypopnea frequency to make a more comprehensive prediction.

In some examples, process 200 can further provide a notification or report including the obstructive sleep apnea indication to the patient. For example, when the obstructive sleep apnea indication is indicative of disordered breathing, the process 200 can provide a notification to a healthcare provider or a hospital. In further examples, when the severity level of the obstructive sleep apnea indication is worse than a predetermined level or the duration of the intermittency is longer than a predetermined time period, the process 200 can provide a notification to the patient and/or a notification to a healthcare provider or a hospital.

FIG. 4 is a block diagram summarizing the example process 200 for obstructive sleep apnea diagnosis. The first step is to perform the HAVOK analysis including two sub-steps: (1) state space reconstruction (see steps 212-216 of the process 200) and (2) forced linear dynamical system representation (see step 218 of the process 200). In particular, a state space is reconstructed from the Hankel matrix to obtain eigen time-delay coordinates using the physiological measurement time series z(t). Consequently, a forced linear system using the eigen coordinates was built to model the linear and chaotic intermittent dynamics. The second step is to perform the intermittency analysis, which includes two steps: (1) intermittent phases and chaotic bursts analysis (see step 218 of the process 200) and (2) spectral analysis and wavelet analysis of the intermittent forcing component (see steps 220 and 222 of the process 200).

Example Noise-Robust Obstructive Sleep Apnea Diagnostic Data

In this section, the numerical validation of the proposed methods is presented on a typical analytical chaotic system, the Lorenz system. The results for the validation include the measure of sensitivity of the Lorenz lobe switching prediction accuracy to the noise level and sampling period, and the intermittency analysis using the $v_r^2$ thresholding from the HAVOK analysis and the CWT thresholding. Subsequently, the implementation of the methods is demonstrated for the OSA example.

Numerical validation on a noise-induced chaotic Lorenz system: The Lorenz system was considered as a canonical example of an analytical chaotic dynamical system with intermittency dynamics, with the addition of Gaussian white noise to perform the sensitivity analysis for the HAVOK model and the disclosed intermittency analysis methods. The governing equations for the noisy Lorenz system are given as follows:

$$\dot{x}_{noisy} = \sigma(y - x) + w_x;$$

$$\dot{y}_{noisy} = x(\rho - z) - y + w_y;$$

$$\dot{z}_{noisy} = xy - \beta z + w_z,$$

where $w = [w_x \ w_y \ w_z] \in \mathbb{R}^3$, $w \sim \mathcal{N}_3(0, Q)$. Q is the process noise covariance matrix:

$$Q = \eta \begin{bmatrix} \sigma_x^2 & \sigma_x \sigma_y & \sigma_x \sigma_z \\ \sigma_x \sigma_y & \sigma_y^2 & \sigma_y \sigma_z \\ \sigma_x \sigma_z & \sigma_y \sigma_z & \sigma_z^2 \end{bmatrix}.$$

For simplicity of the sensitivity analysis, $$Q = \eta I_s \ (\text{i.e.,} \ \sigma_x^2 = \sigma_y^2 = \sigma_z^2 = 1),$$

in which $I_3$ is a 3×3 identity matrix and $\eta$ denotes the noise level. The notion of noise to signal ratio (NSR) can be defined as NSR=$\sigma^2/\mu^2$, where $\mu$ is the signal amplitude and $\sigma^2$ is the time-invariant noise variance. However, due to the dramatic change in the Lorenz state amplitude scale and because the time series obtained by measuring $\dot{x}$ denoted by $$\{\dot{x}_k\}_{k=1}^{n_{samples}}$$

is considered, a more robust estimate of NSR is considered, which is:

$$\widehat{NSR} = Med \left[ \frac{\eta}{\{\dot{x}_k\}_{k=1}^{n_{samples}}} \right],$$

where Med[•] is the median operator that estimates the median of a time series and n is the number of $\dot{x}$ samples. Next, the sensitivity analysis was performed to investigate the uncertainty of the Lorenz lobe switching prediction accuracy induced by the variances in the NSR and sampling rate.

Figures 5A, 5B, 5C, 5D:
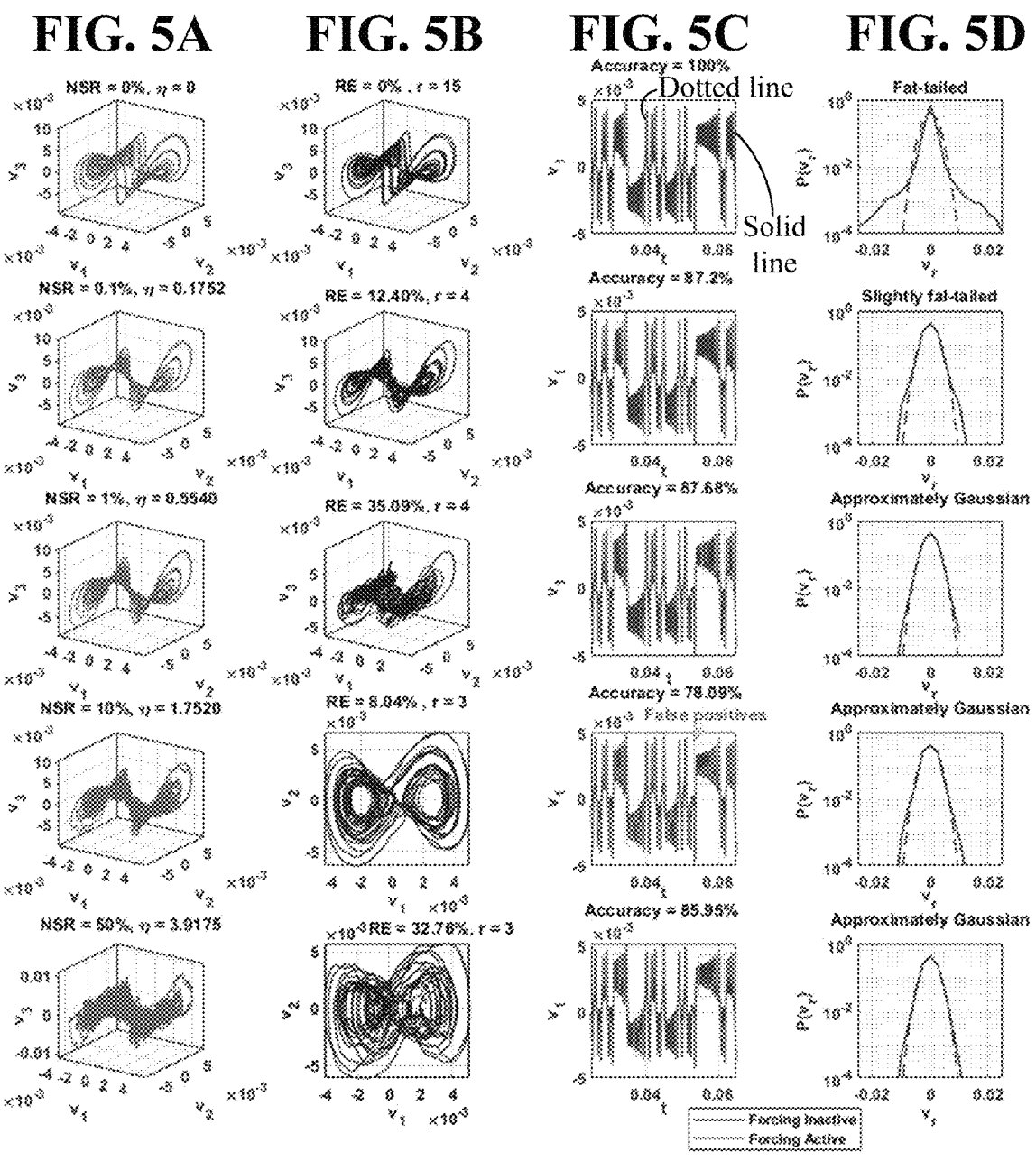
FIGS. 5A-5D illustrate an embedded attractor (FIG. 5A), a reconstructed attractor (FIG. 5B), a lobe switching prediction (FIG. 5C), and a forcing distribution (FIG. 5D) of an example noise-induced Lorenz system with different noise levels according to some embodiments.

Measure of sensitivity of the Lorenz lobe switching prediction accuracy to NSR: The dependence of the Lorenz lobe switching prediction performance on NSR was analyzed by setting the NSR at different levels (0%, 0.1%, 1%, 10%, 50%). The sensitivity analysis results are demonstrated in FIGS. 5A-5D. FIGS. 5A-5D illustrates an embedded attractor (FIG. 5A), a reconstructed attractor (FIG. 5B), a lobe switching prediction (FIG. 5C), and a forcing distribution (FIG. 5D) of an example noise-induced Lorenz system with different noise levels (0%, 0.1%, 1%, 10%, 50%). In FIG. 5A, the Lorenz embedded attractor reconstructed by the first three eigen time-delay coordinates, $v_1$, $v_2$, and $v_3$: the number of rows of the Hankel matrix q=100 (i.e., stackmax=100) is set. In FIG. 5B, the Lorenz reconstructed attractor built from the intermittently forced linear system. The reconstruction error (RE) and the truncated rank, r, values are also provided: the reconstruction error is computed to be the mean absolute percentage error (MAPE) between the first eigen time-delay trajectory, $v_1$, and the reconstructed trajectory, $\hat{v}_1$. The formula is $$MAPE = \frac{100\%}{n} \sum_{k=1}^{n_{samples}} \left| \frac{v_{1,k} - \hat{v}_{1,k}}{v_{1,k}} \right|.$$

In FIG. 5C, the Lorenz lobe switching prediction demonstrated by the $v_1$ trajectory. The active intermittent forcing corresponding to the lobe switching event is dotted lines, and the linear dynamics or inactive forcing is represented by the solid lines, which corresponds to the orbits around one attractor lobe. The prediction accuracy is estimated by the ratio of the sum of true positives and true negatives to the total number of predictions in the test data. The true positives and negatives are the outcomes where the HAVOK model correctly predicts the active forcing and inactive forcing respectively. In FIG. 5D, the $v_r$ forcing distribution, in which fat tails correspond to rare forcing events in the noise-free case, and the approximate Gaussian forcing distributions for the noisy Lorenz system due to white noise.

Figures 6A, 6B, 6C, 6D:
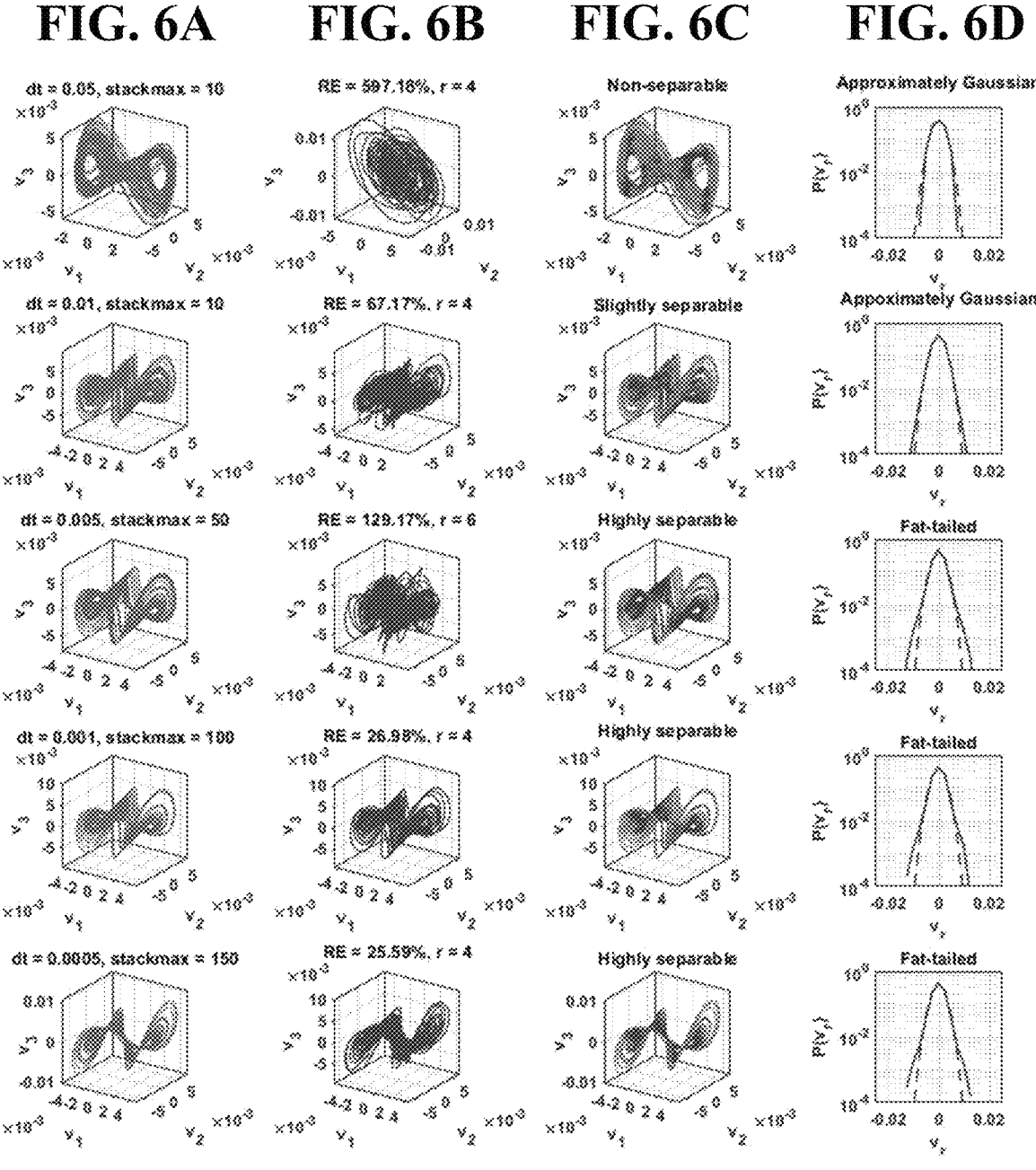
FIGS. 6A-6D illustrate an embedded attractor (FIG. 6A), a reconstructed attractor (FIG. 6B), non-linear regions (FIG. 6C), and a forcing distribution (FIG. 6D) of an example noisy Lorenz system with different sampling periods according to some embodiments.

Measure of sensitivity of the Lorenz lobe switching prediction accuracy to the sampling rate: The dependence of the Lorenz lobe switching prediction performance on NSR was analyzed by setting the sampling period at different values (0.05, 0.01, 0.005, 0.001, 0.0005) with NSR=0.1%. The sensitivity analysis results are presented in FIGS. 6A-6D. FIGS. 6A-6D show an embedded attractor, reconstructed attractor, nonlinear regions, and forcing distribution of the noisy Lorenz system at different sampling periods (0.05, 0.01, 0.005, 0.001, 0.0005) with NSR=0.1%. In FIG. 6A, the Lorenz embedded attractor. The "stackmax" value corresponds to the number of rows, q, of the Hankel matrix. In FIG. 6B, the Lorenz reconstructed attractor, which showed poor reconstruction errors for the first three scenarios (dt=0.05, 0.01, 0.005). In FIG. 6C, nonlinear regions. The trajectories represented by the gray color correspond to small (inactive) forcing or linear dynamics, and the trajectories in red represent active forcing or nonlinear dynamics corresponding to large forcing. The linear and nonlinear regions are well-separated in the last three cases (dt=0.005, 0.001,0.0005). In FIG. 6D, the forcing distributions of $v_r$, which are fat-tailed in the last three scenarios when the nonlinear dynamics are highly separable.

Figures 7A, 7B, 7C, 7D, 7E:
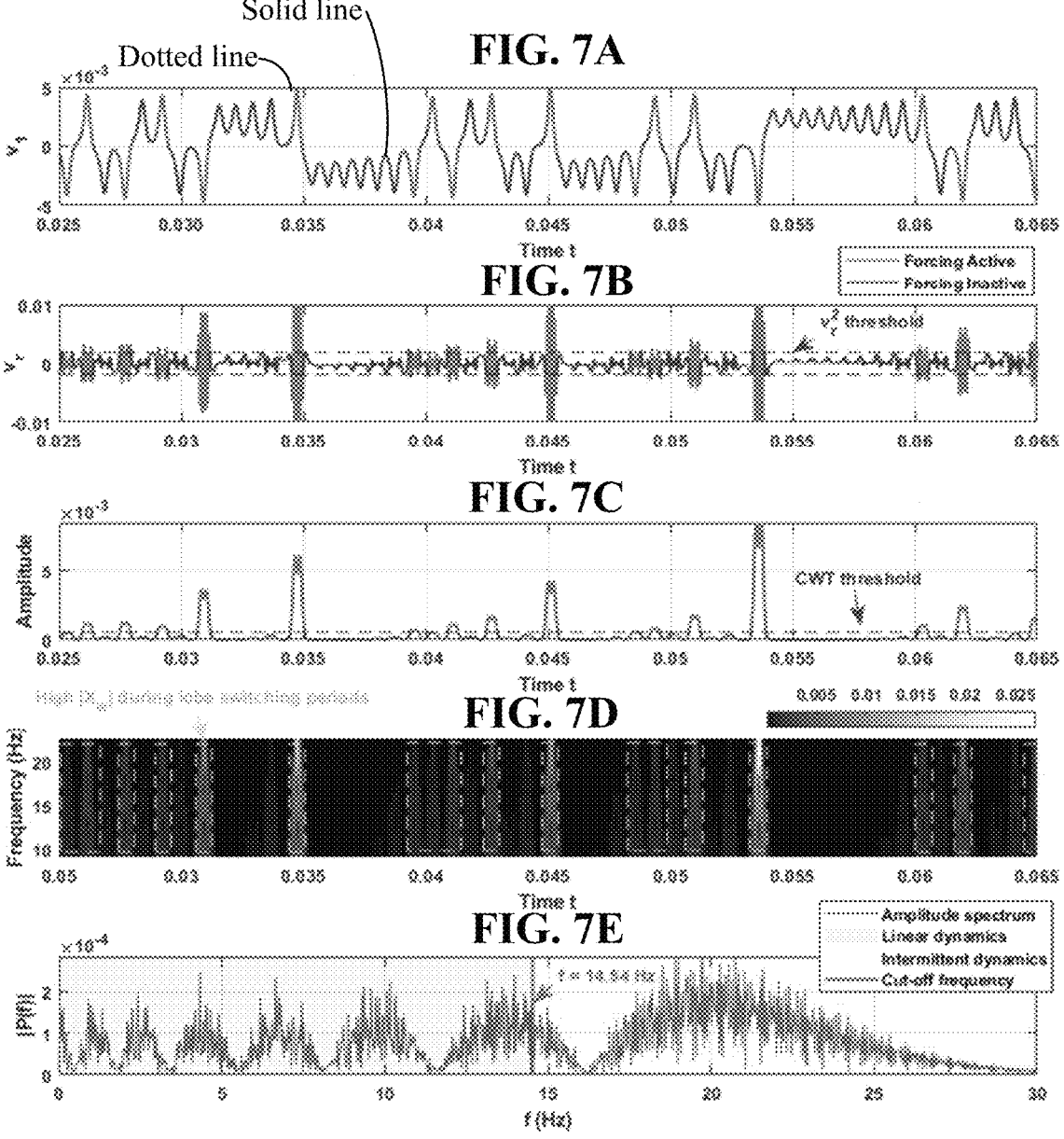
FIGS. 7A-7E illustrate an example Hankel Alternative View Of Koopman (HAVOK) analysis and Intermittency analysis for noise-free chaotic Lorenz system.

Intermittency analysis for the noisy chaotic Lorenz system: To decompose chaos and represent chaos as an intermittently forced linear system, the HAVOK analysis described above was performed. The decomposition of the Hankel matrix provides the eigen time-delay coordinates, and a hard threshold for $$v_r^2$$

was determined for predicting the Lorenz lobe switching events. Afterwards, the spectral analysis and wavelet analysis of the intermittent forcing, $v_r$, were implemented. The results for these steps are summarized in FIGS. 7A-7E. In FIG. 7A, the $v_1$ trajectory, in which the active forcing is the dotted lines, and the inactive forcing is represented by the solid lines. In FIG. 7B, the lobe switching prediction using the $v_r^2$ thresholding (r=15), the period over which $$v_r^2 \geq \psi \max_{v_r(t)}\{v_r^2(t)|t \geq 0\}, \psi = 0.0027$$

is considered the active forcing period. This threshold was chosen by trial and error to optimally separate the linear and nonlinear regions of the Lorenz attractor. In FIG. 7C, the CWT coefficients amplitude $|X_w|$ at the scale $f$=14.54 Hz. The frequency, $f$, and the hard threshold for $|X_w|$ were chosen to yield the best lobe switching prediction accuracy, at 97.34%. In FIG. 7D, the magnitude scalogram of the intermittent forcing, $v_r$, for analyzing $v_r$ at different time and frequency scales, which showed high values of CWT coefficients $|X_w|$ during the lobe switching events. In FIG. 7E, the single-sided amplitude spectrum of $v_r$ that represents the low-frequency region corresponding to linear dynamics and the high-frequency region associated with chaotic dynamics. The frequency that yielded the best prediction accuracy in the CWT thresholding approach serves as the cut-off frequency for the dynamics separation.

To demonstrate the robustness of the intermittency analysis methods for noisy complex systems, the same procedure was applied to the noisy Lorenz system at two different NSR values, 1% and 10%. The results are demonstrated in FIGS. 8A and 8B. HAVOK analysis and intermittency analysis for the noisy Lorenz system at 2 different NSR values, 1% for FIG. 8A and 10% for FIG. 8B. The $v_1$ trajectory by active forcing with dotted lines, the lobe switching prediction using $$v_r^2$$

and CWT thresholding, the scalogram of $v_r$, and the amplitude spectrum of $v_r$ for NSR=1% and NSR=10%. As shown, the CWT thresholding method is more robust to noise than the $$v_r^2$$

thresholding approach: the prediction accuracy estimates using the first method are 95.65% (NSR=1%) and 94.63% (NSR=10%) as opposed to 88.10% (NSR=1%) and 79.82% (NSR=10%) when using the latter method. In addition, the higher the noise level, the lower the prediction accuracy. The scalogram demonstrates the high values of CWT coefficients $|X_w|$ during the lobe switching events, indicated by green lines. The linear and nonlinear dynamics separation in the frequency spectrum is also plotted in the last row.

To characterize the intermittent dynamics, the statistics of intermittent phases and chaotic bursts can be estimated for the Lorenz system as presented above. After the bursts were located, the burst duration statistic was estimated to be $T_b$=0.4121±0.1461, and the inter-burst duration statistic was $T_{ib}$=1.5757±1.4781.

Obstructive Sleep Apnea (OSA) Examples: In some examples of the pathophysiological processes in obstructive sleep apnea (OSA), three steps were performed: (1) signal processing and feature extraction, (2) HAVOK analysis using HRV features, and (3) intermittent forcing analysis using $v_r^2$ thresholding and CWT thresholding.

Signal processing and feature extraction: Signal preprocessing and feature extraction were performed on the electrocardiogram (ECG) signals. First, a $5^{th}$ order Butterworth 0.5-30 Hz bandpass filter was applied to the signal to eliminate noise and baseline wandering. Subsequently, the Hamilton-Tompkins algorithm was employed to detect R peaks and compute RR intervals. A set of 18 features was extracted from Heart Rate Variability (HRV) Tool, an open-source MATLAB Toolbox that quantifies the spectral energy and nonlinear patterns of the HRV signals. Heart rate variability (HRV) features quantify the fluctuation in the time intervals between adjacent heartbeats, which arise from the neurocardiac functions, the heart-brain interactions, and dynamic non-linear autonomic nervous system (ANS) processes. Previous studies have shown that power spectral features extracted from HRV signals are clinically significant for obstructive sleep apnea diagnosis and prediction. Next, the sliding window length was selected to be one minute, corresponding to the 1-minute OSA annotations.

Figures 9A, 9B, 9C:
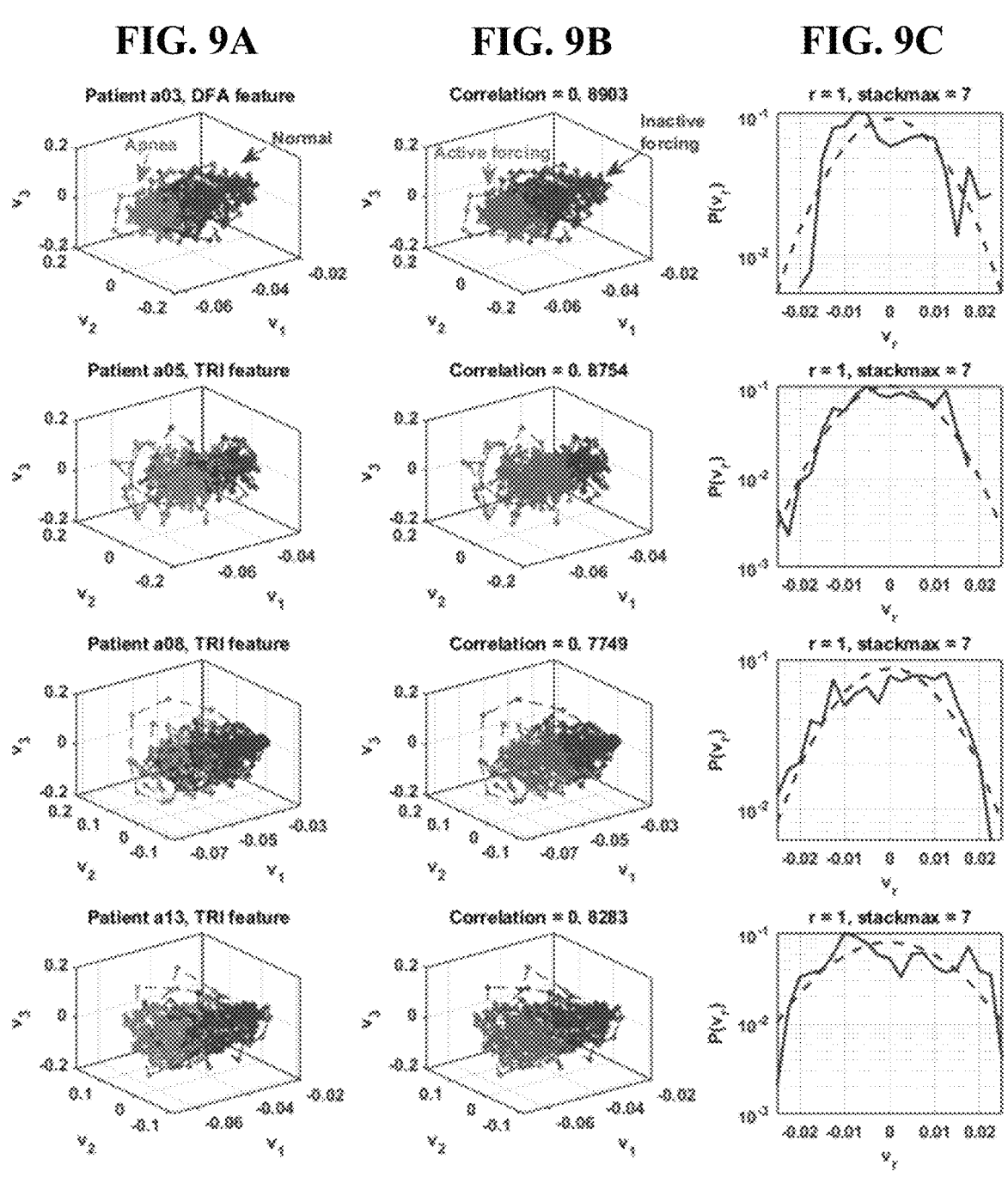
FIG. 9A shows an embedded attractor by obstructive sleep apnea annotation.
FIG. 9B shows an embedded attractor by active forcing.
FIG. 9C shows a forcing distribution.

HAVOK Analysis for the OSA Examples: First, the Hankel matrix, $\mathcal{H}$, of the size q×p was constructed from a measurement (i.e., extracted HRV feature) time series, where q=N−p+1, N is the length of the feature time series, and p is the window length as described above. The q value (i.e., "stackmax" parameter) was chosen such that the maximum periodicity of the underlying dynamics can be captured. The most appropriate HRV feature can be selected to construct the Hankel matrix and obtain eigen-time-delay coordinates v(t). The HAVOK analysis results for 4 representative patients are illustrated in FIGS. 9A-9C. Embedded attractor coded by OSA annotated by the experts and by predicted active forcing, and the forcing distribution of representative patients a03, a05, a08, and a13. In FIG. 9A, the embedded attractor coded by OSA annotations reconstructed by the coordinates $v_1$, $v_2$, and $v_3$ by decomposing the Hankel matrix obtained from a chosen HRV feature. The feature was selected to achieve the strongest correlation (measured by the Pearson correlation coefficient, r) between the active forcing and hypopnea-apnea events. The detrended fluctuation analysis (DFA) feature was chosen for patient a03, while the TRI feature was selected for the other 3 patients. The DFA feature is a method for capturing the statistical self-affinity of the HRV signal, which is useful for analyzing time series that have long-memory processes, while the TRI feature computes the triangular index from the RR-interval histogram. In FIG. 9B, the embedded attractor coded by active forcing. The attractor was also reconstructed from $v_1$, $v_2$, and $v_3$, and the correlation coefficient, r, was reported for comparison. In FIG. 9C, the forcing distributions of $v_r$ (solid line) and the approximate Gaussian (dashed line) in all 4 cases.

Intermittency analysis for the OSA Examples: Next, spectral and wavelet analysis can be performed on $v_r$. The results for two representative patients, a03 and a05, are shown in FIGS. 10A and 10B. FIGS. 10A and 10B show HAVOK analysis and intermittency analysis for representative patients a03 and a05, respectively. For each patient, the 1-minute OSA annotations were plotted corresponding to each 1-minute window of the ECG record. Next, the hypopnea-apnea event prediction results using $$v_r^2$$

and CWT thresholding are presented, followed by the Pearson correlation between the active forcing and the 1-minute OSA annotations. The hard thresholds applied in both methods were determined to maximize the correlation coefficient. Since the slow-time-scale dynamics are considered, the characteristics of the intermittent forcing corresponding to OSA events exhibit high-amplitude waves and low-frequency bursts. The CWT coefficients amplitude $|X_w|$ is plotted at $f$=3.8 mHz and $f$=4.1 mHz for patients a03 and a05 respectively. The frequency, $f$, was chosen to yield the strongest correlation, which is similar to the hard threshold selection method. For both patients, the $$v_r^2$$

thresholding method appears to perform better that the CWT thresholding method. This result can be partially explained by the indistinguishable noisy values of $|X_w|$ that correspond to normal breathing and OSA events depicted in the scalogram of $v_r$. The amplitude spectra of $v_r$, which show that the cut-off frequencies, $f$, were in the "low-energy" region, are also provided for both patients. However, nonlinear and linear dynamics are still not guaranteed to be separable using that cut-off frequency because of the non-desirable correlation coefficient values.

intermittent forcing in 22 OSA patients. Here, the hard threshold is obtained for predicting the intermittent forcing using two methods, namely $$v_r^2$$

thresholding and CWT thresholding; the HRV features used for each approach are also given. The correlation coefficients estimated from the first method are represented by the green bars, and those estimated from the latter are represented by the orange bars. Overall, the $$v_r^2$$

thresholding approach mostly outperforms the CWT thresholding method.

The HAVOK analysis and the intermittent forcing analysis were performed on 22 OSA patients. The results are summarized in Table 1.

TABLE 1

Summary of the HAVOK analysis and the intermittent forcing analysis for 22 OSA patients. Here, the patient ID, their corresponding AHI, the truncated rank, r, the energy captured by intermittent forcing $v_r$, the burst duration $T_b$, and the inter-burst duration $T_{ib}$ can be reported. The overall statistics were estimated for each column.

| Patient ID | AHI | Rank r | #Cols p | $v_r$ energy (%) | $T_b$ in mins (mean ± SD) | $T_{ib}$ in mins (mean ± SD) |
|---|---|---|---|---|---|---|
| a03 | 39.1 | 1 | 7 | 61.23 | 14.80 ± 13.50 | 19.36 ± 16.14 |
| a05 | 41 | 1 | 7 | 67.37 | 26.18 ± 26.88 | 14.40 ± 13.99 |
| a06 | 24.7 | 1 | 7 | 48.64 | 27.83 ± 28.80 | 10.45 ± 7.89 |
| a07 | 63 | 1 | 7 | 37.00 | 48.63 ± 90.48 | 11.14 ± 3.44 |
| a08 | 42 | 1 | 7 | 63.56 | 19.91 ± 15.56 | 23.30 ± 16.17 |
| a11 | 14 | 1 | 7 | 68.87 | 20.58 ± 20.01 | 16.64 ± 21.36 |
| a13 | 42 | 1 | 7 | 65.02 | 19.08 ± 21.69 | 16.36 ± 15.93 |
| a19 | 34 | 1 | 4 | 74.30 | 14.62 ± 10.99 | 25.25 ± 19.21 |
| b03 | 24 | 1 | 4 | 49.22 | 6.64 ± 9.06 | 35.00 ± 25.50 |
| x02 | 37.7 | 1 | 10 | 59.35 | 23.63 ± 20.28 | 28.00 ± 17.16 |
| x05 | 34 | 1 | 10 | 61.37 | 32.80 ± 28.72 | 15.00 ± 11.29 |
| x07 | 21 | 1 | 4 | 73.78 | 11.53 ± 16.92 | 15.50 ± 17.21 |
| x08 | 48 | 1 | 4 | 73.42 | 41.63 ± 33.94 | 22.57 ± 32.25 |
| x09 | 18.5 | 1 | 10 | 53.56 | 28.63 ± 30.83 | 27.86 ± 26.88 |
| x10 | 10 | 1 | 4 | 58.78 | 7.73 ± 9.32 | 41.10 ± 66.80 |
| x13 | 18.7 | 1 | 10 | 53.36 | 34.10 ± 38.58 | 17.22 ± 13.30 |
| x15 | 15.9 | 1 | 16 | 31.53 | 25.29 ± 9.29 | 54.00 ± 28.33 |
| x16 | 24 | 1 | 4 | 65.69 | 7.21 ± 5.34 | 31.15 ± 40.12 |
| x21 | 19 | 1 | 4 | 61.30 | 7.11 ± 9.84 | 19.18 ± 14.81 |
| x23 | 14.3 | 1 | 16 | 34.67 | 60.50 ± 0.71 | 203 ± 0 |
| x25 | 48 | 1 | 7 | 65.69 | 31.44 ± 33.24 | 23.75 ± 27.30 |
| x32 | 15.1 | 1 | 7 | 53.27 | 101.50 ± 105.46 | 28 ± 25.24 |
| Mean ± SI (median) | 29.45 ± 14.14 (24.35) | 1 ± 0 | 7.41 ± 3.50 | 58.23 ± 11.16 (61.27) | 27.79 ± 21.53 (24.46) | 31.74 ± 39.60 (22.94) |

Figure 11:
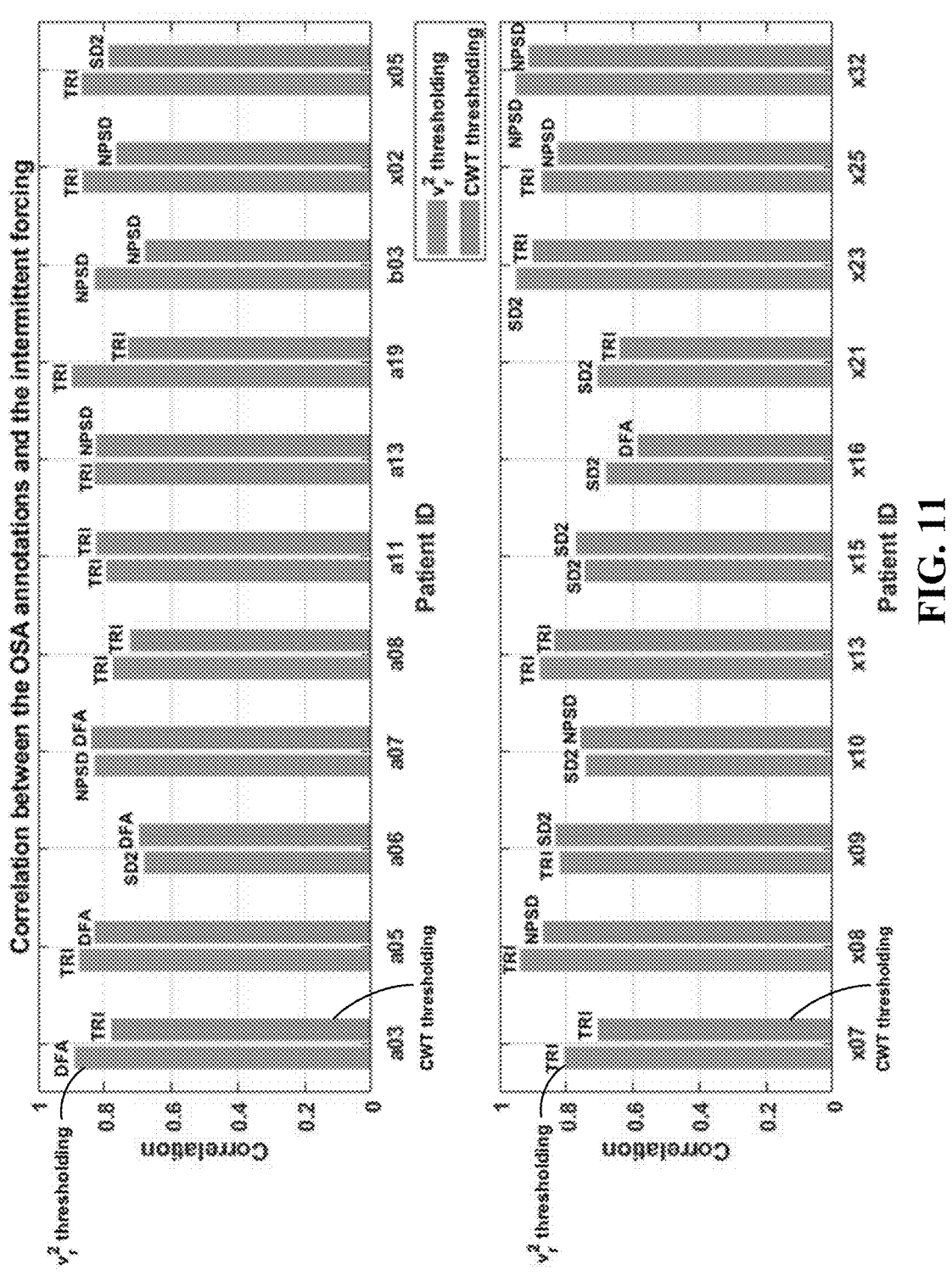
FIG. 11 shows correlation between the obstructive sleep apnea (OSA) annotations scored by an expert and by the intermittent forcing in OSA patients.

To better compare the performance of $$v_r^2$$

and CWT thresholding approaches, the correlation between the OSA annotations and the intermittent forcing was estimated for 22 OSA patients as shown in FIG. 11. Correlation between the OSA annotations scored by an expert and by the According to Table 1, the estimated truncated rank, r, from the SVD of the Hankel matrix was consistently equal to 1, which shows a consistent rank for reconstructing the dynamics. In addition, the percentage of the energy captured by the forcing, $v_r(t)$, which corresponds to the highest energy mode of the dynamics, was 58.23%±11.16 (61.27%) across patients. The pooled means and standard deviations of the burst duration, $T_b$, and the inter-burst duration, $T_{ib}$, were also calculated to be 27.79±21.53 (24.46) minutes and 31.74±39.60 (22.94) minutes, respectively. The inter-patient and intra-patient variances in the estimated pooled statistics are significantly high, which shows the large variation in the burst and inter-burst durations during the apnea-hypopnea events.

Sensor-based and data-driven modeling of the intermittency dynamics in real-life complex systems is challenging because the governing equations are usually unknown. The HAVOK model was proposed to model a chaotic system as an intermittently forced linear system, a method that has been successfully applied to many nonlinear dynamical systems including analytical systems, stochastic magnetic field reversal, and real-world systems. In this disclosure, the noise-robustness of the HAVOK model is validated and a noise-robust intermittency analysis method is developed based on the HAVOK analysis. Therefrom, the intermittent phases, the chaotic bursts, and the spectral-temporal properties of different intermittent dynamics modes are analyzed. Further, the intermittent nonlinear dynamics of obstructive sleep apnea (OSA) is demonstrated as a case study.

Regarding the numerical simulation validation results, the sensitivity of the Lorenz lobe switching prediction accuracy to the noise level and the sampling rate is analyzed. As seen in FIGS. SA-SD, the lobe switching prediction accuracies were 87.20%, 87.68%, 78.09%, and 85.95%, which respectively correspond to the NSR values of 0.1%, 1%, 10%, and 50%. This result is a little counterintuitive because the prediction accuracy did not monotonically decrease as the Gaussian white noise level increased. Interestingly, this result can be explained by the variation in the optimal truncated rank, r, estimated by the optimal rank selection methods. The truncated rank, r, values corresponding to 4 different mentioned NSR values were r=4, r=4, r=3, and r=3; hence, the energy captured by the $v_r$ component was different in each scenario. Moreover, the distribution of the energy for the $v_k$ modes (k=1, . . . q) depends significantly on the Gaussian white noise contamination and the resulting matrix, V, from the Hankel matrix decomposition, which caused the prediction accuracy to fluctuate in response to the amount of energy that $v_r$ captured. The sensitivity of the accuracy may also be partially reflected in the variations in the reconstruction errors that quantify the mean absolute percentage error (MAPE) between the first eigen time-delay trajectory, $v_1$, and the reconstructed trajectory, $\hat{v}_1$, which show that the higher the energy accounted for by $v_1$, the lower the reconstruction error. The contamination by white noise also affected the probability distribution of $v_r$, which caused it to be approximately Gaussian since the high-frequency high-amplitude intermittent bursts were gradually mixed with and then dominated by the broad-frequency-band noise as the NSR is increased. The measure of the sensitivity of the prediction accuracy to the sampling period, dt, demonstrated in FIGS. 6A-6D shows that the dt value must be sufficiently small (i.e., a fine time scale) with an appropriate "stackmax" value to capture the intermittent dynamics and separate the linear and nonlinear regions. The forcing distribution of $v_r$ can be a reliable indicator to determine the identifiability of the intermittent dynamics using the HAVOK model. This result was confirmed by the appearance of the fat-tailed Gaussian distribution after exceeding a certain threshold of dt.

After performing the sensitivity analysis, the intermittency analysis methods using $$v_r^2$$

thresholding and CWT thresholding approaches were performed in the noise-free and noise-induced chaotic Lorenz system. The results from FIGS. 7A-7E, 8A, and 8B demonstrate that the disclosed CWT thresholding method is a more reliable, noise-robust, alternative method to predicting lobe switching events that correspond to the nonlinear dynamics. This result can be confirmed by the low-variance prediction accuracy using the CWT thresholding method (97.34% for the noise-free case, 95.65% when NSR=1%, and 94.63% when NSR=10%). These values for the noisy cases are higher than the values reported when applying the $$v_r^2$$

thresholding method (88.10% when NSR=1% and 79.82% when NSR=10%). The high values of $|X_w|$ showed in the $v_r$ scalogram over the lobe-switching periods demonstrate the active forcing prediction capability of the CWT thresholding. In addition, the $v_r$ frequency spectrum shows the frequency bands associated with the linear dynamics and nonlinear dynamics, in which the linear and nonlinear dynamics regions are separated by a cut-off frequency. This cut-off frequency was chosen to achieve the optimal\lobe switching prediction accuracy. The cut-off frequency is validated by applying a bandpass filter on $v_r$ to filter out the low-frequency components corresponding to the linear dynamics: as a result, only the high-frequency high-amplitude bursts remained in the signal.

The HAVOK analysis using HRV features and the intermittent forcing analysis results for the OSA case study are presented. The embedded attractors shown in FIGS. 9A-9C were coded by both the OSA annotations and the predicted active forcing; and the correlation coefficients between the active forcing and the hypopnea-apnea events of four representative patients were significantly high. This result validates the intermittent forcing identifiability using the disclosed methods and shows a strong association between the active forcing and hypopnea-apnea events. The forcing distributions are approximately Gaussian in all four representative cases, which potentially results from the low sampling period since the HRV features are extracted for each 1-minute time window. Therefore, the HAVOK analysis captures only the slow-time-scale dynamics and not the fast-time-scale dynamics in the Lorenz system, and the forcing distribution is not necessarily fat-tailed. Moreover, the AHI values of all four patients are substantially high (AHI=39.1, 41, 42, and 42), so the hypopnea-apnea events are no longer rare events that contribute to the fat tails of the distribution. The comparison of the $$v_r^2$$

thresholding and CWT thresholding methods is illustrated in FIGS. 10A, 10B, and 11, which show that the $$v_r^2$$

thresholding approach outperformed the alternative method for most of the patients. However, the CWT thresholding method can still be improved by using an adaptive threshold, selecting a more appropriate "mother wavelet," and combining the prediction results at multiple frequencies if the forcing has a broad frequency band and one frequency cannot completely characterize the intermittent dynamics. In FIGS. 10A and 10B, the linear and nonlinear dynamics regions are not separated since the correlation between the active forcing predicted by the CWT thresholding method and OSA events was non-desirable: hence, the validity of the cut-off frequency value could not be justified. From FIG. 11, the correlation coefficients obtained from the CWT thresholding are higher than the those for the other method for patients a06 (AHI=24.7), a07 (AHI=63), a11 (AHI=14), x09 (AHI=18.5), and x10 (AHI=10); interestingly, these AHI values correspond to "mild," "slightly moderate," and "extremely severe" OSA severity cases. A satisfactory explanation for this result requires deeper analysis. Additionally, the correlation values reported for all patients in FIG. 11 confirm the applicability of the HAVOK and intermittency analysis methods for the OSA case study. The means and the variances of the correlation coefficients obtained from the $$v_r^2$$

thresholding and CWT thresholding methods are $0.8288\pm0.0813$ and $0.7776\pm0.0831$ respectively.

The intermittent phase and chaotic burst statistics were estimated for both the Lorenz system and the OSA case study. For the Lorenz system, the burst duration statistics were estimated to be $T_b=0.4121\pm0.1461$, and the inter-burst duration statistics were computed to be $T_{ib}=1.5757\pm1.4781$. The burst duration that corresponds to the lobe switching period has fairly low variance; however, the inter-burst duration has significantly high variance, which indicates the spontaneous occurrence of the lobe switching events in the Lorenz chaotic system. With regard to the OSA case study, the burst duration and inter-burst duration statistics varied dramatically from patient to patient, which can be attributed to inter-patient variability in terms of the OSA conditions and the cardiovascular comorbidities' causing the major differences in the intermittent dynamics. The fluctuations in the inter-patient statistics may correspond to different intermittent behaviors arising from a mixture of hypopnea and different types of apnea: obstructive apnea, central apnea, and complex apnea. Despite the high inter-patient variations in the statistics for the intermittent phases and chaotic bursts, the truncated rank, r, was consistently equal to 1 for all patients, and the percentage of the energy captured by $v_r$ was $58.23\%\pm11.16$, which is a relatively low variance. This result indicates that the highest energy mode is suitable for capturing the active forcing that results from the slow-time-scale dynamics. The validation of this finding in other case studies (e.g., paroxysmal atrial fibrillation or an epileptic seizure) is highly necessitated. In this case study, the selected HRV features reflect the activities and effects of a mixture of both sympathetic and parasympathetic systems, e.g., vagal-mediated modulation of heart rate. However, HRV features can be insufficient to provide information about respiration-related paroxysmal events such as hypopnea-apnea events; therefore, many studies have combined HRV features with ECG-derived respiratory signals (EDR) to improve the richness of the features and the model accuracy. In some examples, the intermittent forcing signal obtained from the Hankel matrix built from the HRV features captures the long-time-scale dynamics of the sympathetic and parasympathetic effects, but more investigation into this hypothesis is necessary.

When applying the HAVOK model, the selection of model hyperparameters should be carefully considered. First, the number of rows, q, in the Hankel matrix should be selected to obtain an appropriate delay embedding basis, U, and the time delay, $\tau$, should be chosen based on the embedding dimension, p, to enforce the independence of the time series. The truncated rank, r, can be estimated by the optimal hard threshold for singular values. However, in principle, the eigen time-delay variables can be separated into r−s high-energy modes for the linear model and s low-energy intermittent forcing modes if $v_r(t)$ is not sufficient to model the intermittent forcing. In addition, the high model performance sensitivity to hard threshold selection in the $$v_r^2$$

and the CWT thresholding methods can be alleviated by adopting an adaptive thresholding method, selecting a more appropriate "mother wavelet." and combining the prediction results at multiple frequencies if the forcing has a broad frequency band.

In summary, the disclosed system and method provide an intermittency analysis method that systematically decomposes and analyzes the intermittent forcing obtained from the HAVOK model. The disclosure provides (1) numerical validation of the HAVOK model's robustness with respect to the noise level and sampling rate, (2) a noise-robust intermittency analysis framework to characterize the intermittent phases, the chaotic bursts, and the spectral-temporal properties of different intermittent dynamics modes, and (3) an attempt to characterize chaos in pathophysiological processes as an intermittently forced linear system and thoroughly analyze the intermittent forcing. In particular, in addition to the distribution of the intermittent forcing, additional statistics such as burst starting-ending time and burst and inter-burst duration quantifiers to better characterize the intermittent phases and chaotic bursts are disclosed. Moreover, the frequency spectrum of the intermittent forcing signal estimated from the Discrete Fourier transform were used to characterize the spectral properties of the intermittent forcing. The adaptive continuous-time wavelet analysis with different types of mother wavelets chosen to match the morphological features of the bursts was performed to extract local spectral and temporal information simultaneously. To validate the disclosed methods, the intermittency analysis methods were performed on both the Lorenz system and an OSA case study. This is the first attempt in the literature to characterize chaos in pathophysiological processes in a sleep disorder like OSA. In the OSA case study, the forcing signal can predict the intermittent transient events, such as the transition from normal to hypopnea-apnea episodes. Spectral decomposition and wavelet analysis of intermittent forcing was used to investigate the composition of the forcing terms, which is potentially related to the long time-scale dynamics of the sympathetic and parasympathetic effects regulated by the human bodies. An understanding of intermittent dynamics facilitates the development of interpretable and robust domain-knowledge, data-driven methods for complex systems that exhibit intermittent and chaotic behaviors.

Example Noise-Robust Sampling

Several sampling strategies have been introducing, including burst sampling, delay spacing, and iterative modeling, which were designed to optimally collect data for SINDy and HAVOK models in various noise-free multi-scale systems. However, there were several limitations: (1) the data-sampling strategies lack robustness, which were designed and evaluated for noise-free scenarios, (2) the specification of parameters, such as sampling period, burst size, and burst locations for burst sampling strategy, is challenging when system dynamics are not well understood and poses the problem of adaptability, (3) the proposed sampling strategies are heuristic sampling methods, which are not supported a formalized underlying theory, and (4) it is difficult to scale up to high-dimensional systems, where the complexity and computational demands increase significantly. Hence, it motivates the development of efficient, noise-robust, scalable algorithms for optimal sampling strategies to address the limitations of the foregoing methods.

In addressing the identified limitations in existing data sampling methods, the disclosure introduces an innovative approach incorporating the SINDY algorithm with a deep Q-learning agent within a reinforcement learning framework to design a noise-robust optimal data sampling strategy for multi-scale complex systems discovery. The disclosed method is designed to overcome the forementioned limitations through three key innovative elements: adaptability, robustness, and scalability. Firstly, it employs an adaptive sampling strategy that leverages reinforcement learning. Unlike traditional uniform-sampling strategies, the disclosed approach can dynamically modify the sampling policy based on the evolving multi-scale dynamics of the system. This innovation ensures greater accuracy and efficiency in data acquisition by catering to the specific demands of the system at any given point in time. Secondly, the disclosed approach incorporates a novel design for the state space, observation space, and reward signals, which is grounded on active learning principles and information theory. The design aims to minimize the impact of noise, model output variance, generalization error, and solution instability on model identification and reconstruction. This element enhances the robustness of the disclosed method, ensuring that the disclosed methodology can withstand and adapt to different types and levels of uncertainties and instabilities. Lastly, the disclosed method and system use a deep Q-learning algorithm that is capable of scaling to high-dimensional systems. This feature significantly broadens the utilization of the method to model complex system types irrespective of their dimensionality. This innovation, therefore, addresses a major limitation of previous methods and establishes the disclosed methodology as a novel solution in the field. Two analytical systems are chosen as numerical studies to validate the disclosed methods: (1) Two coupled fast and slow Vander Pol oscillators, and (2) a noisy fast Van der Pol oscillator coupled with a noisy slow Lorenz system. These cases were selected as they collectively represent a range of complexities and challenges in multi-scale dynamics and provide a comprehensive assessment of the disclosed method's effectiveness.

Two-time-scale deterministic coupled systems: The disclosure focuses on the complex systems that exhibit dynamics on multiple time scales. A simplified version of such multi-scale systems that features linear coupling and two distinct time scales can be defined as: $\tau_{fast}\dot{u}=f(u)+Cv$, and $\tau_{slow}\dot{v}=g(v)+Du$, where $\tau_{fast}$ and $\tau_{slow}$ are two parameters that control the time resolution of the fast and slow dynamics, $u(t)\in \mathcal{M}_u\equiv\mathbb{R}^n$ and $v(t)\in \mathcal{M}_v\equiv\mathbb{R}^l$ are the set of "fast"

and "slow" variables on two manifolds $\mathcal{M}_u$ and $\mathcal{M}_v$ respectively, $f(\bullet)$ and $g(\bullet)$ are the "fast" and "slow" flow map operators. The linear coupling effects between u and v are represented by the matrices $C\in\mathbb{R}^{n\times l}$ and $D\in\mathbb{R}^{l-n}$, which captures the coupling between the fast and slow dynamics of the complex system. The time scale separation can be quantified by the ratio $\phi\tau=\tau_{slow}/\tau_{fast}$, between the "fast" and "slow" scales of u and v. This simplified system serves as a starting point for the development of the disclosed reinforcement learning-based data sampling strategy aiming to capture the multi-scale dynamics in a more general context.

The disclosed method includes two computational components: the SINDy algorithm for multi-scale model discovery and the reinforcement learning framework for the optimal sampling strategy. The SINDy algorithm to discover the multi-scale models is introduced. Via the algorithm, the behavior of complex systems across multiple scales can be predicted. The disclosure details how to formulate the problem, develop the sparse regression, and discover the governing equations. The reinforcement learning framework focuses on the design and optimization of sampling strategy. The process of data sampling is desirable for the success of any data-driven model, and the use of reinforcement learning techniques can effectively sample high-dimensional complex spaces. The reinforcement learning framework section can be divided into several subsections: an overview of the framework, the environment, action, and state spaces definitions, the reward signal and terminal conditions, and the reinforcement learning algorithm employed. Together, the disclosed frameworks can handle the challenges of multi-scale interpretability and high dimensionality of complex systems.

SINDy algorithm for multi-scale model discovery: Based on the extant SINDy algorithm, this algorithm can be extended to search for a parsimonious model that approximates the multi-scale dynamics $f(\bullet)$ and $g(\bullet)$, represented by the functions $\hat{f}(\bullet)$ and $\hat{g}(\bullet)$. The estimated functions contain only a few active terms (i.e . . . they are sparse in a basis of possible candidate functions) corresponding to predominant dynamics. In this framework, the model discovery problem is cast as a sparse regression problem, in which the snapshots of system states (u, v) and their derivatives ($\dot{u}$, $\dot{v}$) are available or computed from data. The snapshots are usually stacked to form two data matrices X and $\dot{X}$ sampled at different time points $t_1, t_2, \ldots, t_m$ as follows:

$$X = \begin{bmatrix} u(t_1) & \ldots & u(t_m) \\ v(t_1) & \ldots & v(t_m) \end{bmatrix}^T = \begin{bmatrix} u_1(t_1) & \ldots & u_n(t_1) & v_1(t_1) & \ldots & v_l(t_1) \\ u_1(t_2) & \ldots & u_n(t_2) & v_1(t_2) & \ldots & v_l(t_2) \\ \vdots & \ddots & \vdots & \vdots & \ddots & \vdots \\ u_1(t_m) & \ldots & u_n(t_m) & v_1(t_m) & \ldots & v_l(t_m) \end{bmatrix}$$

$$\dot{X} = \begin{bmatrix} \dot{u}(t_1) & \ldots & \dot{u}(t_m) \\ \dot{v}(t_1) & \ldots & \dot{v}(t_m) \end{bmatrix}^T = \begin{bmatrix} \dot{u}_1(t_1) & \ldots & \dot{u}_n(t_1) & \dot{v}_1(t_1) & \ldots & \dot{v}_l(t_1) \\ \dot{u}_1(t_2) & \ldots & \dot{u}_n(t_2) & \dot{v}_1(t_2) & \ldots & \dot{v}_l(t_2) \\ \vdots & \ddots & \vdots & \vdots & \ddots & \vdots \\ \dot{u}_1(t_m) & \ldots & \dot{u}_n(t_m) & \dot{v}_1(t_m) & \ldots & \dot{v}_l(t_m) \end{bmatrix}$$

where X, $\dot{X}\in\mathbb{R}^{m\times(n+l)}$. Next, a library $\Theta(X)$ of K possible candidate functions (e.g., constant, polynomial, and trigonometric functions) is constructed, in which each column corresponds to one function:

$$\Theta(X) = \begin{bmatrix} | & | & | & | & | & | & | & | \\ 1 & X & X^2 & X^3 & \ldots & \sin(X) & \cos(X) & \ldots \\ | & | & | & | & | & | & | & | \end{bmatrix}$$

Based on the "sparsity" assumption for $f$ and g, the SINDy algorithm applies the thresholded least squares method to learn a sparse coefficient vector $\Xi$: $=[\xi_1 \; \xi_2 \; \ldots \; \xi_{n+l}]\in \mathbb{R}^{K\times(n+l)}$ which indicates which nonlinear terms are active. The sparse regression problem is given as: $\dot{X}=\Theta(X)\Xi$. Once $\Xi$ has been learned, the governing equations can be discovered as follows:

$$\dot{u}_1 = \Theta(x)\xi_1, \quad \dot{u}_2 = \Theta(x)\xi_2, \quad \ldots, \quad \dot{u}_n = \Theta(x)\xi_n$$

$$\dot{v}_1 = \Theta(x)\xi_{n+1}, \quad \dot{v}_2 = \Theta(x)\xi_{n+2}, \quad \ldots, \quad \dot{v}_l = \Theta(x^T)\xi_{n+l}$$

where $\Theta(x)$ is a vector of symbolic functions of elements of $x=[u^T \; v^T]$.

Reinforcement learning framework for optimal sampling strategy. To address the challenge of optimal sampling in multi-scale model discovery, a reinforcement learning (RL) framework can be adopted.

Figure 12:
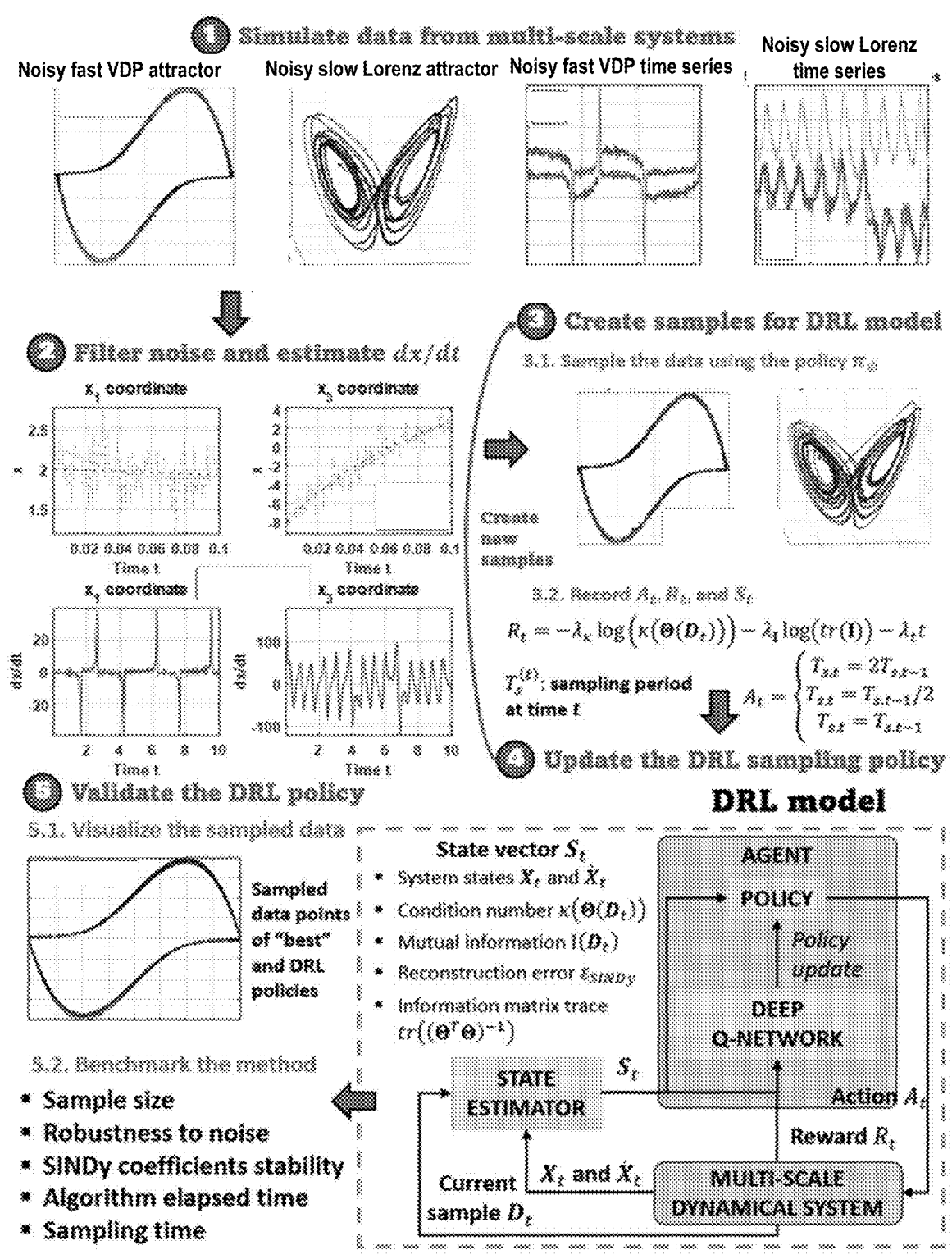
FIG. 12 shows a schematic diagram of an example Deep Reinforcement Learning (DRL) framework for optimal sampling strategy according to some embodiments.

The disclosure describes a new deep reinforcement learning (DRL) framework to establish an optimal sampling strategy capable of sampling the data for discovering multi-scale system dynamics. The block diagram of the proposed methods consisting of 5 steps is illustrated in FIG. 12. FIG. 12 shows a schematic illustration of the disclosed Deep Reinforcement Learning (DRL) framework for optimal sampling strategy. This diagram illustrates the five steps involved: (1) data simulation from multi-scale complex systems, (2) noise filtering from state measurements and derivative estimation, (3) and (4) creating training samples from data simulation and update the policy iteratively update until terminal conditions are met, and finally (5) benchmarking the developed policy against other methods. FIG. 12 also depicts the formulation of the DRL environment, including the action space, state space, and reward function, demonstrating how each plays a significant role in the learning process. It serves as a visual guide to understanding the intricate workflow and interactions within the proposed DRL framework.

In the disclosed DRL framework for optimal sampling strategy, the first step includes data simulation from multi-scale complex systems. An adaptive Runge-Kutta method can be employed to solve the system's ordinary differential equations and subsequently introduce Gaussian noise to simulate real-world uncertainties. For real-life systems with state measurements from sensors, complete datasets or employ state estimation techniques are directed used, such as Kalman filter or particle filter, for incomplete data. Additionally, based on observed real-life data, a "digital twin" environment simulator is created. This simulator, modeled after the actual system using techniques like system identification, serves as a controlled training ground for the DRL agent, ensuring the strategies developed are adaptable and robust for both simulated and real-world scenarios. Next, a low-pass filter can be used to reduce the noise with high frequencies and estimate the state derivatives dx/dt, where $x=[u^T \; v^T]$, via the explicit fourth-order central finite difference scheme [46]. For the highly noise-distorted state measurements, the total variation regularized derivative estimation methods can provide more accurate derivative estimates. The third and fourth steps develop training experiences for the RL agent to learn the sampling policy, which is for generating the SINDy algorithm's training data. The last step is to benchmark the policy $\pi_\psi(s)$ obtained from DRL framework against other methods in terms of sample size, robustness to noise, stability of the estimated parameters, and sampling time. The environment is a multi-scale deterministic coupled system, incorporating the sampling period $T_s$ and the state space S. The action space $\mathcal{A}$ consists of three potential actions: up-sampling, down-sampling, or maintaining. The actions adjust $T_s$ based on the system's states and the current sample characteristics, generating an intermediate reward $R_t$. The state space includes the reconstruction error $\varepsilon_{SINDy}$, the condition number $\kappa(\Theta(D_t))$, the multivariate mutual information of $I(D_t)$, and the trace of the information matrix $tr((\Theta^T\Theta)^{-1})$. The reward signal, integral to improving the SINDy algorithm's convergence, is a weighted sum of 3 components: $\kappa(\Theta(D_t))$, $tr((\Theta^T\Theta)^{-1})$, and the current system time t. The terminal conditions are based on a tolerance rate or when the number of training episodes surpasses predetermined threshold $n_{eps}$. In real-world complex systems, where $\Xi^*$ is generally unknown, the condition number's convergence can serve as an alternative criterion for determining the terminal condition.

Environment: Following the overall framework, the environment component governs the optimal sampling policy learning process. Without loss of generality, the environment is defined as a two-time-scale deterministic coupled system corrupted by Gaussian noise to represent real-world uncertainties and random fluctuations. The system dynamics are characterized by two different temporal scales-fast and slow-representing the behavior of two sets of variables, respectively denoted as u(t) and v(t). The mathematical form of the deterministic coupled system with two distinct timescales, corrupted by the Gaussian noise, is expressed as follows:

$$\tau_{fast}\dot{u} = f(u) + Cv + \varepsilon_u$$

$$\tau_{slow}\dot{v} = g(v) + Du + \varepsilon_v$$

where $\varepsilon_u\in \mathbb{R}^n$ and $\varepsilon_v\in \mathbb{R}^l$ represent the Gaussian noise affecting each of the states in u(t) and v(t) respectively. Each of these noise terms is modeled as a multivariate Gaussian distribution with zero mean and a covariance matrix, which means $$\left(0, \eta_u^T I_n\right)$$

where $I_k$ denotes the identity matrix of size k, and $\eta_u\in \mathbb{R}^n$ and $\eta_v\in \mathbb{R}^l$ represent the variances of the noise associated with the "fast" and "slow" variables, respectively. To quantify the impact of this noise on the dynamics of the system, the concept of the noise-to-signal ratio (NSR) can be introduced for each state variable. The NSR is calculated as the ratio of the variance of the noise (noise power) to the expected power of the signal, which provides a measure of the relative strength of the noise in comparison to the signal, serving as a factor in the design and evaluation of the sampling policy. Thus, the NSR for the state variable $x\in u\bigvee v$ is defined as $NSR:=\eta_x/\mathbb{E}[x^2]$, where $$\mathbb{E}[x_i^2]$$

and $\eta_x$ are the expected value of x and the variance of the state x. A higher NSR indicates that the noise power is high compared to the signal power, which can make it more challenging for the RL agent to learn an optimal sampling policy. In contrast, a lower NSR suggests that the signal power dominates over the noise power, making it potentially easier for the RL agent to learn from the system's dynamics.

Action space $\mathcal{A}$: For the disclosed deep RL framework, a discrete action space $\mathcal{A}$ can be defined such that the discrete action space includes three possible actions. The choice to employ a discrete action space instead of a continuous one originates from the practical nature of the optimal sampling strategy task for the multi-scale dynamics discovery, in which the sampling periods typically use adjustments by integer multiples to capture the dynamics across various scales. Such changes are well-represented through a discrete action space, which consists of simple and definite actions such as doubling, halving, remaining the current sampling period. These discrete actions are computationally efficient and easy to implement, making the task of managing and discovering multi-scale dynamics more streamlined and manageable. Each action alters the sampling period, $T_s$, thereby influencing the multi-scale dynamics of the system. At each transition, the three possible sampling actions $A_t \in \mathcal{A}$ are: (1) $A_t=1$ (double $T_s$ for downsampling). (2) $A_t=0$ (remain the same $T_s$), and (3) $A_t=-1$ (halve $T_s$ for up-sampling). At each transition, the sampling action $A_t$ decides the location of the next sampled point of X. The initial sample in X is $x_0$, and the initial sampling period $T_0$ is pre-specified. These actions are mathematically represented as:

$$A_t = \begin{cases} T_{s,t+1} + 2T_{s,t} & \text{if } A_t = 1 \wedge 2T_{s,t} \geq T_{high} \\ T_{s,t+1} = T_{s,t} & \text{if } A_t = 0 \\ T_{s,t+1} + \dfrac{T_{s,t}}{2} & \text{if } A_t = -1 \wedge \dfrac{T_{s,t}}{2} \leq T_{low} \end{cases}$$

In the equation above, the effects of each action are conditioned by the current sampling period and the thresholds $T_{low}$ and $T_{high}$, which are the lower and upper limits of $T_s$, respectively. The action space $\mathcal{A}$ is a component that directly drives the evolution of the system dynamics through the sampling strategy, affecting the learning process of the agent. In the subsequent sections, other significant components of the reinforcement learning framework (e.g., the state space, the reward function, the terminal conditions, and the RL algorithm for updating the optimal sampling policy) exist. The interactive component of the environment, the "sampling action" $A_t$, carries out three potential tasks. Each action directly influences the sampling period $T_s$, subsequently modifying the multi-scale dynamics that the system experiences. These actions are not arbitrary: instead, they are driven by the current sample characteristics and the system states. As a response to these actions, an intermediate reward $R_t$ gets generated, which guides the learning process of the agent. This generated reward gives feedback on the efficiency of the sampling strategy, thus informing the learning agent on how to refine its future decisions. Next, the characteristics of the state space, and reward signal are described in detail below.

State space S: The state space defines the input variables for the Deep Q-network that approximate the state-action-value function Q(s,a). The space S can include the SINDy reconstruction error $\varepsilon_{SINDy}$, the condition number [48], $\kappa(\Theta(D_t))$, of the matrix $\Theta(D_t)$, where $D_t$ is the current sample of X after the transition t, the multivariate mutual information $I(D_t)$, and the trace of the information matrix (i.e., inverse of the variance matrix) $tr((\Theta(D_t)^T\Theta(D_t))^{-1})$. The state space can be defined to include the important input variables that can approximate well the state-action-value function Q(s,a). Table 1 presents a description of each of these variables, which illustrates their notations, mathematical formulations, and the functions within the state space. From direct representations of system dynamics to measurements of information sharing and algorithmic performance, these variables collectively facilitate effective approximation of the state-action-value function Q(s,a).

TABLE 2

| Description of the variables in the RL state space for multi-scale dynamics discovery | | | |
|---|---|---|---|
| State variables | Notation | Mathematical formulation | Description |
| System states and derivatives | $X_t$ and $\dot{X}_t$ | $X_t = [u]^T(t)\ v^T(t)]$ $\dot{X}_t = [\dot{u}^T(t)\ \dot{v}^T(t)]$ where u(t) and v(t) "fast" and "slow" variables at time t | These variables serve as the elements of the system's dynamics. |
| SINDy reconstruction error | $\varepsilon_{SINDy}(D_t)$ | $\varepsilon_{SINDy} := \|\hat{\Xi}_{D_t} - \Xi^*\|_F^2$ where $\hat{\Xi}_t$ and $\Xi^*$ are the estimated and true sparse coefficient vectors, and $\|\cdot\|_F$ is the Frobenius norm operator. | The SINDy algorithm uses a thresholded least squares method to find sparse coefficient vectors $\Xi := [\xi_1]\ \xi_2 \ldots \xi_K]$ that solves the sparse regression problem $\dot{X} = \Theta(X)\Xi$, |
| Condition number | $\kappa(\Theta(D_t))$ | $\kappa(\Theta(D_t)) := \sigma_{max}(\Theta)/\sigma_{min}(\Theta)$ where $\sigma_{max}(\Theta)$ and $\sigma_{min}(\Theta)$ are the maximum and minimum singular values of the matrix $\Theta$ | The condition number of $\Theta$ can quantify the stability of the estimated $\hat{\Xi}_t$ after solving $\dot{X} = \Theta(X)\Xi$ |
| Multivariate mutual information | $I(D_t)$ | $I(X_1, X_2, \ldots, X_N) = \Sigma I(X_i) - \Sigma I(X_i, X_j) + \ldots + (-1)^n I(X_1, X_2, \ldots, X_N)$ | It measures the amount of information shared by the samples in $D_t$ |

TABLE 2-continued

| Description of the variables in the RL state space for multi-scale dynamics discovery | | | |
| --- | --- | --- | --- |
| State variables | Notation | Mathematical formulation | Description |
| Information matrix trace | $tr((\Theta^T\Theta)^{-1}) \equiv tr(I)$ | $tr\left((\Theta^T\Theta)^{-1}\right) = tr(I) = \sum_{i=1}^{n} I_{ii}$ <br><br> where I is the information matrix and $I_{ii}$ denotes the diagonal elements of I. | The trace of the inverse of the information matrix I computes the average variance of $\hat{\Xi}_t$ |

The state space variables are carefully selected based on their relevance to the optimal sampling task. System states and derivatives ($X_t$ and $\dot{X}_t$) provide real-time understanding of the system dynamics, helping predict future evolution and guide optimal sampling decisions. SINDy reconstruction error $\varepsilon_{SINDy}(D_t)$ quantifies the algorithm's performance, informing the agent about the quality of the sparse coefficient vector approximation. Condition number $\kappa(\Theta(D_t))$ serves as an indicator of the stability of the solution, alerting the agent to sensitivity in the sparse regression problem and prompting it to seek stability-enhancing actions. Multivariate mutual information $I(D_t)$ measures the mutual dependence among the samples, guiding the agent to maintain diversity in sampling and optimize the solution. Lastly, the trace of the information matrix $tr(I)$ offers an estimate of the uncertainty inherent in the sparse coefficient vector estimation, which encourages the agent to minimize this uncertainty. Each of these components contributes vital information to the state space S, enhancing the agent's ability to make informed and effective decisions.

Reward signal and terminal conditions: In some examples, the reinforcement learning is to maximize a cumulative reward, which serves as a measure of the agent's success in achieving its goal. In the disclosed framework, the reward signal is designed to encourage the efficient discovery of multi-scale dynamics while maintaining stability and precision in the sparse coefficient estimation. The reward function is formulated as: $R_t=-\lambda_\kappa \log(\kappa(\Theta(D_t))-\lambda_I \log(tr(I)-\lambda_t t$, where $\Delta_\kappa$, $\Delta_I$, and $\lambda_t$ are the non-negative weights that balance the importance of the three terms: $\log(\kappa(\Theta(D_t))) \log(tr(I))$, where $$I = \left(\Theta(D_t)^T \Theta(D_t)\right)^{-1},$$

and the current system time t. The disclosed framework's reward signal formulation can address the challenges of multi-scale dynamics discovery, with each component representing a distinct objective. The logarithm of the condition number $\log(\kappa(\Theta(D_t)))$, a measure of a matrix's sensitivity to errors, is included in the reward to encourage stability of the SINDy algorithm, as lower condition numbers lead to more stable coefficient estimations. The logarithm transforms the multiplicative condition number into an additive factor, compatible with the additive nature of Q-values in RL, while inversely associating high condition numbers with lower rewards. For the $\log(tr(I))$ term, the high trace of the information matrix $tr(I)$, indicating the inverse of the average variance of the sparse coefficient estimates $\hat{\Xi}_t$ at the time t, can be penalized. By inversely associating high trace with lower rewards, the RL agent is motivated to explore dynamic and diverse samples, leading to greater variability in the multi-scale system dynamics. The direct inclusion of the current system time t promotes the efficiency with actions facilitating faster discovery of multi-scale dynamics leading to shorter time periods and higher rewards. Together, these components target the stability, the dynamical variability, and the efficiency with weighting factors $\lambda_\kappa$, $\lambda_I$, and $\lambda_t$ providing a mechanism to fine-tune the reward function based on specific problem requirements, which adds an extra layer of versatility to the RL framework.

In terms of terminal conditions, an episode terminates when the number of training episodes exceeds the predefined limit $E_{max}$ or when the reconstruction error of the SINDy model $\varepsilon_{SINDy}$ falls below a certain threshold $\varepsilon_{tol}$. First, the incorporation of $E_{max}$ guarantees computational feasibility and reflects the real-world constraints, which compels the agent to find an optimal strategy within a finite timeframe. Second, the terminal condition based on $\varepsilon_{SINDy}$ aligns with an objective to achieve a precise sparse dynamical model. This error measures the discrepancy between the sparse dynamical system derived from the data sampled by the agent and the true underlying dynamical system. When this error falls below the threshold $\varepsilon_{tol}$, it signifies that the agent has collected enough useful data samples that yield an accurate model of the system's dynamics. Thus, the episode knowing that the agent has accomplished its objective can be terminated. However, in real-world scenarios, the rare access to the true sparse coefficient vectors $\Xi^*$ of complex systems makes it impossible to evaluate $\varepsilon_{SINDy}$ directly. In such cases, the convergence of the condition number $\kappa(\Theta(D_t))$ can be an alternative criterion. The condition number measures the stability of the estimated sparse coefficient vectors after solving the sparse regression problem. A converging condition number suggests that the regression solution has stabilized, which implies the agent's data sampling has become effective enough to capture the underlying dynamics. Thus, it is a practical and viable indicator of when the agent should terminate the episode. In summary, these terminal conditions are designed to guide the agent towards a robust and efficient learning process, even when dealing with complex real-world systems.

Figure 13:
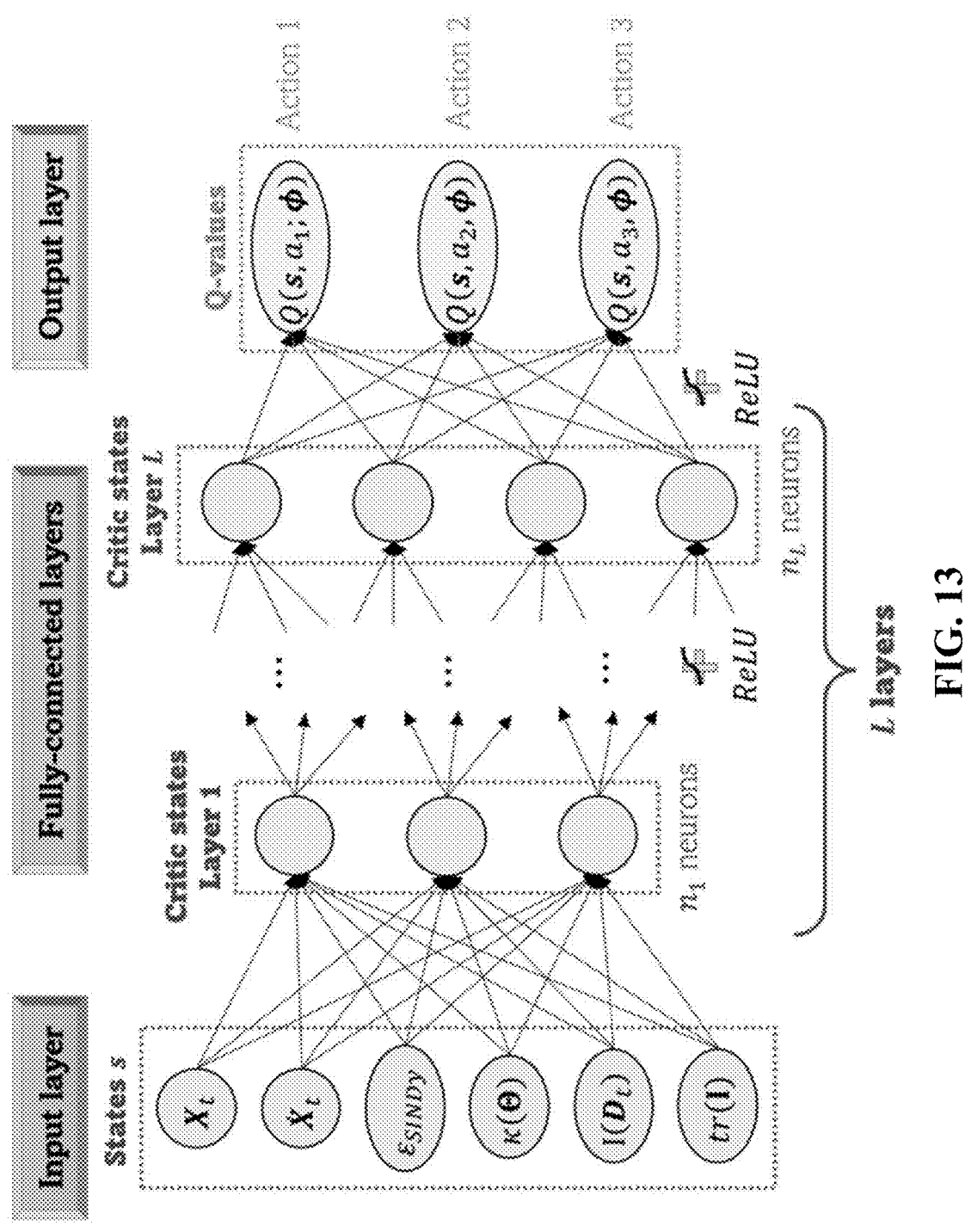
FIG. 13 shows a schematic neural network architecture according to some embodiments.

Deep Q-network agent creation and training: In the disclosed methodology, the next stage is the creation and training of the DQN agent. A deep Q-network algorithm can be used to design an optimal sampling policy. As a variant of Q-learning, the DQN agent serves as a reinforcement learning component trained to maximize the expected cumulative reward and accomplish efficient sampling in a two-time-scale deterministic coupled system corrupted with Gaussian noise. The creation of the DQN agent involves initializing the critic and target critic that will approximate the value function. Here, the critic is denoted as $Q(s, a; \phi)$ and the target critic as $Q_t(s_t, a_t; \phi_t)$, where $\phi$ and $\phi_t$ are the critic parameters. The critic and target critic are created as deep neural networks that map the environment states and selected sampling action to the expected cumulative reward. The schematic architecture of the deep Q-network is illustrated in FIG. 13. FIG. 13 shows a schematic neural network architecture for the DQN agent. The architecture starts with an input layer that involves the states of the environment, followed by L fully connected layers that represent critic states with $n_k$ (k=1, . . . , L) nodes each. Both fully connected layers utilize ReLU activation functions. The network's output layer corresponds to the Q-values for each action in the action space.

Following the initialization of these critic function approximators, the configuration of the DQN agent is performed. The DQN agent is designed to adopt an epsilon-greedy exploration strategy during its training phase. Here, at each decision point, the agent either randomly explores a new action with a probability E, or exploits the action that maximizes the current value function with a probability of 1−ε. This strategic balance of exploration and exploitation aids in the robust and comprehensive learning of the optimal sampling policy within the noise-infused environment. In the training phase of the DQN agent, the Q-Learning algorithm that is tailored to the environment with its specific multi-scale deterministic coupled system and noise characteristics is implemented. At each training time step, the agent selects an action a according to its current state s, and the action a is subsequently executed resulting in an immediate reward r and a new state observation s'. This sequence creates totally $n_t$ experience tuples $$\{(s_i, a_i, r_i, s_i')\}_{i=1}^{n_t}, \text{ where } (s_i, a_i, r_i, s_i')$$

represents the $i^{th}$ sampled experience tuple, which will be stored in a circular buffer known as the experience replay buffer. A mini-batch of experiences is then sampled randomly from this buffer to provide the data for updating the value function targets $Q^*(s_i, a_i)$. If the sampled next state $s_i'$ is a terminal state, $Q^*(s_i, a_i)$ is set to the immediate reward $r_i$. Otherwise, derived from the Bellman equation, the following equation is computed: $Q^*(s_i, a_i)$ as:

$$Q*(s_i, a_i) = R_i + \gamma Q_t \left( s_i', \underset{a}{\text{argmax }} Q(s_i', a; \phi); \phi_t \right).$$

Here, $Q^*(s_i, a_i)$ represents the expected cumulative reward or the true Q-value for taking action $a_i$ in state $s_i$, $\gamma$ is the discount factor and $$\underset{a}{\text{argmax }} Q(s_i', a; \phi)$$

represents the best action at $$s_i'$$

according to the critic's current parameters $\phi$. In the training phase, by comparing this $Q^*(s_i, a_i)$ with the Q-value approximated by the neural network $Q(s_i, a_i; \phi)$, the critic's approximations are iteratively redefined to the optimal Q-values that represent the true expected returns. The critic's parameters $\phi$ are then updated by minimizing the mean squared loss between $Q'(s_i, a_i)$ and $Q(s_i, a_i; \phi)$ over all experiences in the sampled mini-batch as follows:

$$\mathcal{L}(\phi) = \frac{1}{2M} \sum_{i=1}^{M} (Q*(s_i, a_i) - Q(s_i, a_i; \phi))^2,$$

where M is the size of the mini-batch. After $\phi$ is updated, the target critic parameters $\phi_t$ are estimated based on the selected target update method, which may include smoothing, periodic, or periodic smoothing techniques. Concurrently, as training progresses, the probability threshold $\varepsilon$ is gradually reduced for choosing a random action. This is adjusted according to a pre-defined decay rate, balancing the exploration and exploitation dynamics during the learning process. Hence, the DQN agent is trained to learn the optimal sampling policy by considering the intricate dynamics of the multi-scale deterministic coupled system and its inherent noise properties.

3.2.7. RL-based and heuristic approaches for finding the optimal sampling policy. After the establishment and training of the DQN agent, the RL algorithm can be implemented for seeking the optimal sampling policy. This algorithm is specifically formulated to work in conjunction with the trained DQN agent and leverages the knowledge acquired during the training phase. The purpose of this RL algorithm is to navigate the unique complexities of the multi-scale deterministic coupled system and utilize this understanding to produce a parametrized sampling policy that optimizes the chosen reward function, even in the presence of inherent noise. The reinforcement learning algorithm for finding the optimal sampling policy is outlined as Algorithm 1 below:

---

Algorithm 1: Reinforcement learning for SINDy optimal sampling policy in noisy multi-scale complex systems

---

1 Input: A, S, $E_{max}$, $\eta_u$, $\eta_v$, $T_s^{init}$, $\varepsilon_{tol}$, $x_0$, $\Xi^*$, $\Theta$, $max_{iter}$, N, $\lambda_\kappa$, $\lambda_f$, and $\lambda_t$
2 Output: optimized RL-based parametrized sampling policy $\hat{\pi}_\psi{}^*(s)$
3 Initialize environment:
4 Initialize parameters to build the environment
5 Create DQN agent specifying network architecture and hyperparameters
6 Set training options (maximum training episodes $E_{max}$ and stopping criteria)
7 for i ∈ {1, ... , $E_{max}$} do
8 | Reset the environment:
9 | Sample initial data $D_t = \{x^{(k)}\}_{k=1}^{n_{D_t}}$ starting at $x_0$ with $T_s^{init}$, f(u), g(v),
  | where x = $[u^T \ v^T]$
10 | Introduce Gaussian noise to x(t) and $\dot{x}(t)$ with noise levels $\eta_u$, $\eta_v$:

Algorithm 1: Reinforcement learning for SINDy optimal sampling
policy in noisy multi-scale complex systems 11 | $\tilde{x}(t) \leftarrow x(t) + \varepsilon_u, \tilde{\dot{x}}(t) \leftarrow f(x(t)) + \varepsilon_v, \varepsilon_u \sim \mathcal{N}(0, \eta_u{}^2 I_n),$
   | $\varepsilon_v \sim \mathcal{N}(0, \eta_v{}^2 I_l)$
12 | Estimate $\hat{\Xi}_t$ and $\varepsilon_{SINDy,t}$ from $\tilde{x}(t), \tilde{\dot{x}}(t)$ using SINDy algorithm $\varepsilon_{SINDy,t}$
   | $\leftarrow \|\hat{\Xi}_t - \Xi^*\|_F^2$
13 | while ($\varepsilon_{SINDy,t} < \varepsilon_{tol}$) and ($n_{iter} < \max_{iter}$) do
14 | | $n_{iter} \leftarrow n_{iter} + 1$
15 | | Select action $a_t \in \mathcal{A}$ at current state s using $\varepsilon$-greedy policy
   | | derived from critic $Q(\cdot)$
16 | | Update sampling period $T_s$ according to action $a_t$ using Equation
   | | (3.6)
17 | | Update t according to action $a_t$, $t \leftarrow t + T_s$
18 | | Sample new $\tilde{x}(t)$ and $\tilde{\dot{x}}(t)$ from noisy multi-scale system and
   | | append them to $D_t$
19 | | Estimate new $\hat{\Xi}_t$ and $\varepsilon_{SINDy,t}$ using SINDy algorithm
20 | | Calculate states $\kappa(\Theta(D_t))$, $tr(I)$, and $I(D_t)$
21 | | Calculate intermediate reward $r_t$ using Equation (3.7)
22 | | Store experience (s, $a_t$, $r_t$, s') in buffer B
23 | | Sample mini-batch of experiences from B and compute target $y_i$
24 | | Update critic parameters $\phi$ by minimizing loss function in Equation
   | | (3.9)
25 | | Every N steps, update target critic parameters $\phi_t = \phi$
26 | | Update current state: s' $\leftarrow$ s
27 | end
28 end
29 Return optimized sampling policy $\hat{\pi}_\psi{}^*(s)$, where $\Psi$ is generic parameters
   of DQN network In the disclosure, apart from the RL-based approach (Algorithm 1), 2 other algorithms are developed for finding the optimal sampling policy (Algorithms 1S and 2S in SI file), which are provided in the supplementary file. These methods are the benchmarks to evaluate the performance of the RL-based strategy. Algorithm 1S employs a randomized brute-force search to determine the optimal sampling policy. The central premise of this method is the execution of M simulations, each implementing a different random sampling strategy $\pi_i$, where the action for the current state is selected randomly. After the terminal conditions are satisfied, the algorithm evaluates the performance of each policy $\pi_i$ by calculating the loss function $\mathcal{L}(\pi_i)$, and the optimal sampling policy is obtained by selecting the best $\pi_i$ that minimizes $\mathcal{L}(\pi_i)$. In Algorithm 2S, a greedy sampling method can be used for finding the optimal sampling policy. This method differs from the first two by continuously choosing the best available action, driven by a defined optimality-criteria function $\Phi(D_t)$ based on optimal design theory. Unlike Algorithm 1S, which randomly selects an action, this method samples the new data within the search range $\Delta_s$ according to the optimality-criteria $\Phi(D_t)$. After the terminal conditions are met, the optimal sampling policy can be acquired. In addition to those 3 algorithms, the traditional uniform sampling strategy was utilized for comparison. The uniform sampling strategy operates under a fixed sampling rate, disregarding the state of the system. Therefore, its limitation lies in its inability to adapt to the state dynamics, making it potentially sub-optimal when dealing with systems that exhibit complex, multi-scale behaviors. The disclosed method with the RL-based and heuristic sampling strategies provides the benefits of adaptive, state-aware sampling in dealing with the unique challenges posed by the multi-scale deterministic coupled system.

Comparative analysis of sampling strategies in multi-scale complex systems: To demonstrate the efficacy and versatility of the disclosed reinforcement learning-based approach for optimal sampling policy in complex systems, a series of experiments were conducted across two numerical studies. Thus, an evaluation of the performance of the disclosed approach is performed and the disclosed approach is contrasted against the other proposed sampling strategies: randomized brute-force search, greedy sampling, and the traditional uniform sampling method. The chosen numerical studies represent multi-scale complex systems, specifically, the coupled fast and slow Van der Pol oscillator and a noisy fast Van der Pol oscillator coupled with a noisy slow Lorenz system. Both these systems present distinct complexities and challenges that make them ideal for a thorough assessment of the various sampling strategies.

The evaluation can start by setting up each experiment and determining the appropriate parameters for the system under examination. Next, the four different sampling strategies were applied to the system. Consistency is maintained in the approach while other factors were kept constant to allow for a fair comparison. The application of each strategy was methodically carried out, and the results were documented. Subsequently, the results were synchronized to evaluate the performance of each strategy on each system. This was done by assessing 6 evaluation metrics: sample size n, $\varepsilon_{SINDy}$, $\log(\kappa(\Theta(D_{T_{train}})))$, $\log(tr(I(D_{T_{train}})))$, total training time $T_{train}$, and total elapsed time of the sampling algorithm $T_{elapsed}$, Where $D_{T_{train}}$ is the final sample obtained when the SINDy sampling process converges. Firstly, the sample size n provides an insight into the quantity of data points used by the algorithm to accurately identify the system's dynamics. A smaller sample size generally indicates greater data efficiency of the sampling process. $\varepsilon_{SINDy}$ represents the error associated with the SINDy model, reflecting the accuracy of the identified models. The evaluation metric $\log(\kappa(\Theta(D_{T_{train}})))$ measures the condition number of the matrix associated with the sampled data, which plays a critical role in determining the stability and reliability of the system identification process. $\log(tr(I(D_{T_{train}})))$ quantifies the trace of the information matrix for the sampled data, serving as an indicator of the data's informative content. Total training time $T_{train}$ is a direct measure of the computational cost associated with the training process using the sampled data. Lastly, total elapsed time of the sampling algorithm $T_{elapsed}$ offers an overview of the efficiency and speed of the sampling algorithm itself.

Example 1: Two noisy coupled Vander Pol oscillators: In this example, the example 2 coupled fast and slow Van der Pol oscillators described by the following system of ordinary differential equations (ODEs) is considered:

$$\tau_{fast}\dot{x}_1 = x_2 + c_1 x_3 + \varepsilon_{u_1}$$

$$\tau_{fast}\dot{x}_2 = \mu_1(1 - x_1^2)x_2 - x_1 + \varepsilon_{u_2}$$

$$\tau_{slow}\dot{x}_3 = x_4 + c_2 x_1 + \varepsilon_{v_1}$$

$$\tau_{slow}\dot{x}_4 = \mu_2(1 - x_3^2)x_4 - x_3 + \varepsilon_{v_2}$$

The variables $x_1$ and $x_2$ represent the fast dynamics, while $x_3$ and $x_4$ represent the slow dynamics of the system. The parameters $c_1$ and $c_2$ serve to couple the two dynamical systems, the time constants $\tau_{fast}$ and $\tau_{slow}$ differentiate the fast and slow dynamics, respectively. Here, $\varepsilon_{u_1} \sim \mathcal{N}(0, \eta_u)$, $\varepsilon_{u_2} \sim \mathcal{N}(0, \eta_u)$, $\Sigma_{v_1} \sim \mathcal{N}(0, \eta_v)$, and $\varepsilon_{v_2} \sim \mathcal{N}(0, \eta_v)$ are Gaussian noise terms with zero mean added to each of the state variables to reflect the presence of noise and uncertainty. The noise levels $\eta_u$ and $\eta_v$ are set in accordance with the chosen noise-to-signal ratio (NSR) for each experiment. The initial condition was set as $x_0=(2,0,0,2)$, the coupling constants $c_1=0.005$, $c_2=1$, the coefficients $\mu_1=\mu_2=5$, and the time constants $\tau_{fast}=0.2$, $\tau_{slow}=1$.

Figures 14A, 14B, 14C:
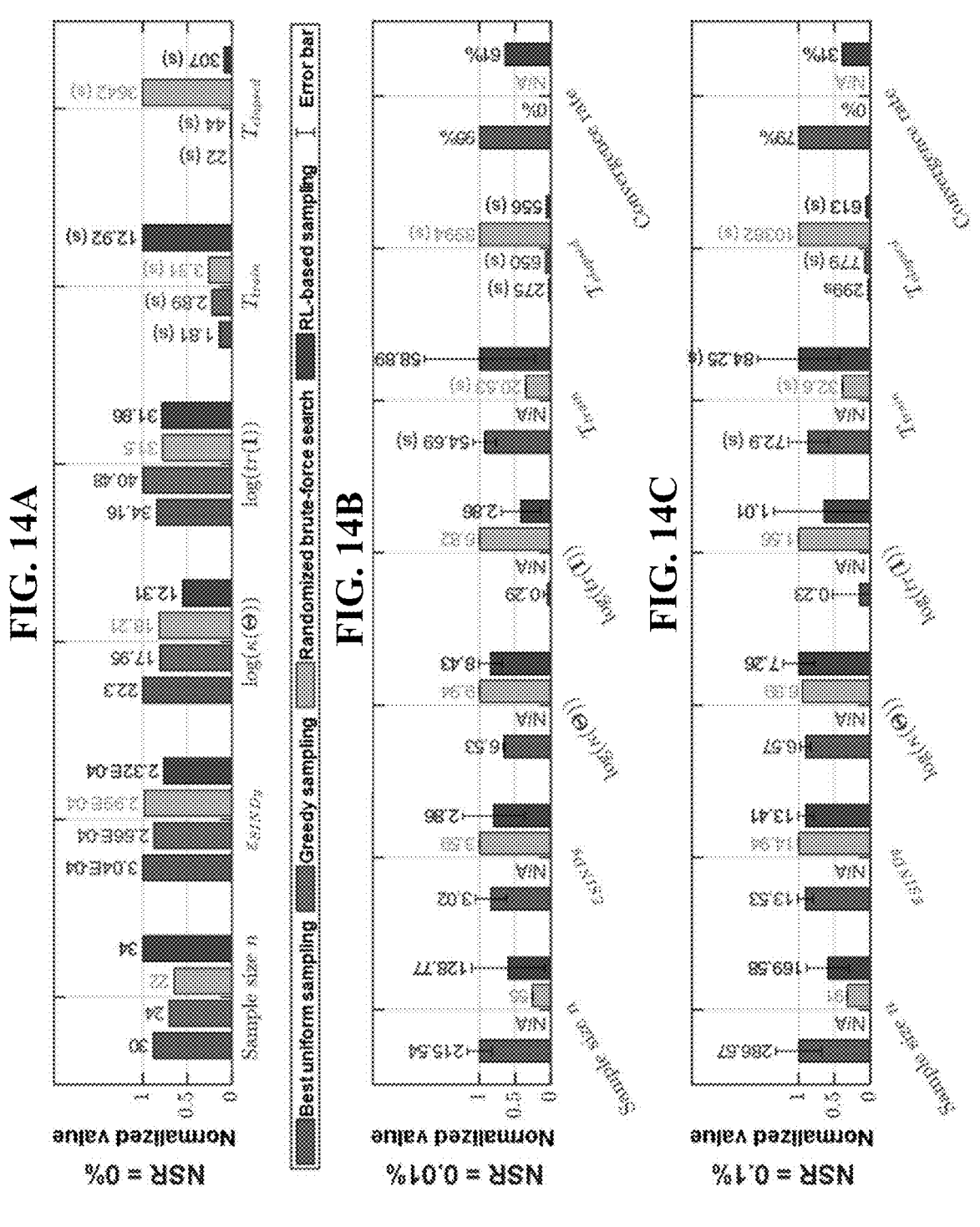
FIGS. 14A-14C shows comparative analysis of different sampling strategies with a noise-free scenario in FIG. 14A, low noise conditions in FIG. 14B, and moderate noise conditions in FIG. 14C.

Implementing and evaluating the sampling policies: Given the system dynamics and initial settings outlined above, 4 distinct sampling strategies were implemented and compared for the two coupled Van der Pol oscillator systems, namely: (1) Uniform Sampling, (2) Greedy Sampling, (3) Brute-Force Search, and (4) Reinforcement Learning (RL), under three levels of Noise-to-Signal Ratios (NSR)-0%, 0.1%, and 1%. The results of these comparisons are presented in FIGS. 14A-14C. FIGS. 14A-14C show comparative analysis of 4 different sampling strategies under 3 noise-to-signal ratio (NSR) settings. FIG. 14A shows noise-free scenario (NSR=0%), FIG. 14B shows low noise conditions (NSR=0.1%), and FIG. 14C shows moderate noise conditions (NSR=1%). In FIG. 14A, 6 sampling policy evaluation metrics were considered: sample size n, $\varepsilon_{SINDy}$, $\log(\kappa(\Theta(D_{T_{train}})))$, $\log(tr(I(D_{T_{train}})))$, total training time $T_{train}$, and total elapsed time of the sampling algorithm $T_{elapsed}$, Where $D_{T_{train}}$ is the final sample obtained when the SINDy sampling process converges. For the noisy systems represented in FIGS. 14B and 14C, an additional metric was introduced called convergence rate, defined as the percentage of simulations among 100 simulations where the SINDy sampling process converges under noise conditions. The error bars represent the standard deviations of the metric values across 100 simulation runs.

In the noise-free environment (NSR=0%, FIG. 14A), the sample size varied significantly across the four methods. The brute-force search resulted in the smallest sample size of 22, showcasing its efficiency in sample minimization, despite its extensive computational demand. The uniform and RL-based strategies produced a slightly larger sample size (30 and 34, respectively), while the greedy sampling strategy achieved an even smaller sample size of 24. Regarding the accuracy of learned dynamics measured by $\varepsilon_{SINDy}$ all strategies demonstrated comparably low values, suggesting that they could accurately capture the system dynamics. Remarkably, the RL-based strategy achieved the lowest $\varepsilon_{SINDy}$ value, signifying superior learning accuracy despite its moderately larger sample size. The $\log(\kappa(\Theta))$ and $\log(tr(I))$, indicative of the diversity and information content of the samples, were highest for the uniform sampling strategy, followed by the RL-based strategy, and then the greedy sampling strategy. The brute-force search fell last in this metric, signaling less diverse sampling. When considering the computational time, the uniform sampling strategy proved to be the most efficient, with the shortest $T_{elapsed}$, whereas the brute-force search was the most computationally demanding.

In FIG. 14B, when NSR=0.1%, the uniform and RL-based strategies maintained high convergence rates of 95% and 61%, respectively. Despite the increased noise level, both methods effectively learned the system dynamics as reflected in the relatively low $\varepsilon_{SINDy}$ values. However, the sample sizes used by these methods increased markedly compared to the noise-free scenario. On the other hand, the greedy sampling method, which performed well under noise-free conditions, could not be evaluated due to the inability to ensure convergence in the presence of noise. This result underscores the sensitivity of the greedy method to noise disturbances. Upon further increase of the noise level to NSR=1%, the convergence rates for the uniform and RL-based strategies dropped to 79% and 31%, respectively. The RL-based method exhibited a larger $\varepsilon_{SINDy}$ value and used an increased sample size, indicating that learning the system dynamics became more challenging in the presence of higher noise. Yet, it maintained a reasonably low $\log(\kappa(\Theta))$ and $\log(tr(I))$, highlighting the diversity of the samples collected. On the other hand, the uniform sampling method used a larger sample size but displayed a considerably larger $\varepsilon_{SINDy}$, which signifies compromised learning accuracy under high noise conditions.

Figures 15A, 15B, 15C, 15D, 15E, 15F:
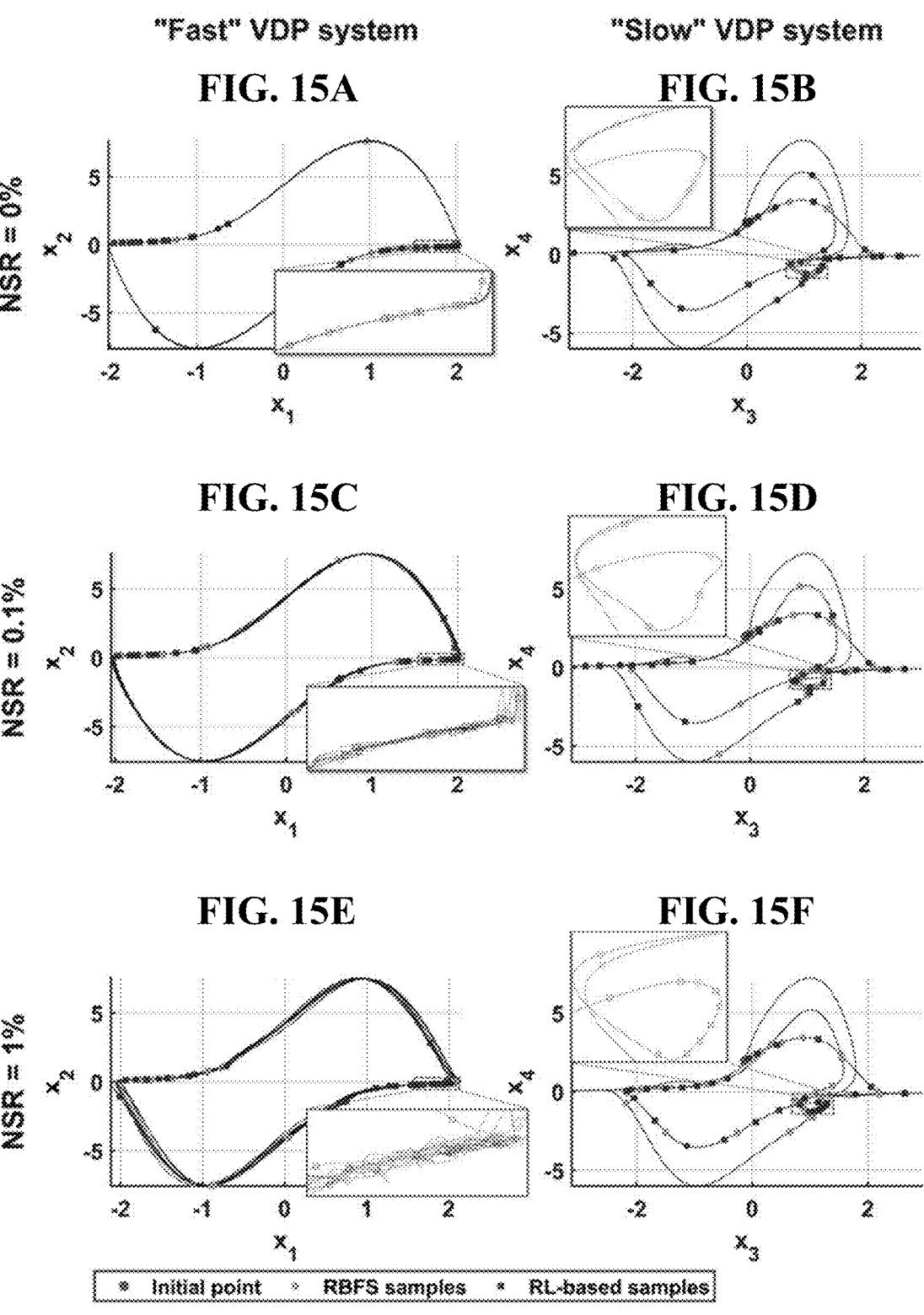
FIGS. 15A-15F show visualization of samples obtained from an example sampling strategy, where

To further illuminate the effectiveness of the disclosed sampling strategies in adapting to varying noise levels, the samples obtained by the most effective strategy are visually represented—the randomized brute-force search, as well as the RL-based sampling policy. FIGS. 15A-15F provide a comprehensive view of the sampling patterns of both strategies under three noise scenarios (NSR=0)%, 0.1%, and 1%), revealing their robustness and adaptability. As illustrated, each strategy is tasked with capturing the dynamical behavior of both the fast and slow VDP systems under varying noise conditions, offering an interesting perspective on their functionality. FIGS. 15A-15F show visualization of samples obtained from the best sampling strategy—randomized brute-force search (RBFS) and the RL-based sampling policy under varying noise conditions for the coupled "fast" and "slow" Van der Pol (VDP) systems. FIGS. 15A, 15C, and 15E depict the samples for the fast VDP system under NSR settings of 0%, 0.1%, and 1% respectively. FIGS. 15B, 15D, and 15F mirror these NSR settings for the "slow" VDP system. In each scatter plot, the squares represent samples obtained from the RL-based method, and the circles represent samples obtained from the RBFS. The black trajectories were reconstructed from the simulated samples derived from solving ODEs of the coupled "fast" and "slow" VDP systems. The box depicts the high-resolution of the trajectories and samples.

FIGS. 15A-15E visualize the similarities in the sampling strategies of the randomized brute-force search (RBFS), deemed as the optimal approach, and the RL-based sampling policy under varying noise conditions for the coupled fast and slow Van der Pol (VDP) systems. In the noise-free scenario (NSR=0%), FIGS. 15A and 15B, both the RL-based and the randomized brute-force search methods primarily maintained or doubled $T_s$, reflecting a mutual understanding of the system's dynamics and confirming the RL-based approach's strategy in mimicking the optimal strategy. For the low noise level (NSR=0.1%), shown in FIGS. 15C and 15D, the RL-based policy's adaptability became evident. It mirrored the RBFS strategy of maintaining or doubling the sampling period for the fast and slow dynamics. This indicates the RL-based method's ability to adjust to system complexity changes, matching the sampling actions of the optimal approach. With a further increase in noise level to NSR=1%, the RL-based sampling policy continued to mirror the optimal approach effectively, as seen in FIGS. 15E and 15F. Both strategies primarily maintained or doubled the sampling period, reflecting their adaptability to the increased system complexity introduced by higher noise levels.

In addition, the Van der Pol (VDP) system is a nonlinear oscillator that exhibits a limit cycle behavior, which means that its state variables oscillate around a stable equilibrium. In the VDP system, there is an "excitation" or "bursting" region characterized by rapid changes in the system's state variables. This region typically occurs when the system is initially perturbed or excited and can exhibit chaotic or irregular behavior. On the other hand, the "limit cycle" region is characterized by slower oscillations, where the dynamics are more predictable and less chaotic. In FIGS. 15A-15F, both RBFS and RL-based sampling approaches align with the inherent properties of the VDP system. In the limit cycle region, the system exhibits periodic oscillations, thereby necessitating more frequent sampling for an accurate depiction of the system dynamics. On the contrary, the transient region is characterized by a rapid movement towards the limit cycle, which may not necessitate a dense sampling strategy due to its short duration and quick convergence to the stable state. Therefore, it highlights the method's ability to capture and adapt to the complexities of multi-scale dynamical systems.

Example 2: A noisy fast Van der Pol oscillator coupled with a noisy slow Lorenz system: In this example, a more complex coupled system that involved a fast Van der Pol oscillator and a slow Lorenz system was considered. The Van der Pol oscillator represents a system with nonlinear dynamics and a limit cycle, while the Lorenz system, famous for its butterfly-like chaotic behavior, introduces an additional level of complexity. The interplay between the oscillatory behavior of the fast dynamics and the chaotic behavior of the slow dynamics makes the problem more challenging and provides a robust test for the sampling algorithms. The coupled system of differential equations was as follows:

$$\tau_{fast}\dot{x}_1 = x_2 + c_1 x_3 + \varepsilon_{u_1}$$

$$\tau_{fast}\dot{x}_2 = \mu_1\left(1 - x_1^2\right)x_2 - x_1 + \varepsilon_{u_2}$$

$$\tau_{slow}\dot{x}_3 = \sigma(x_4 - x_3) + c_2 x_1 + \varepsilon_{v_1}$$

$$\tau_{slow}\dot{x}_4 = x_3(\rho - x_5) - x_4 + \varepsilon_{v_2}$$

$$\tau_{slow}\dot{x}_5 = x_3 x_4 - \beta x_5 + \varepsilon_{v_3}$$

The system parameters included the coupling constants $c_1$=0.01, $c_2$=10, the coefficients $\sigma$=10, $\rho$=28, $\beta$=8/3, and $\mu$=5. The choice of these parameters was made to ensure that the system dynamics remain interesting and non-trivial, while the influence of both the fast and slow variables is significant. Here, $\varepsilon_{u_1} \sim \mathcal{N}(0, \eta_u)$, $\varepsilon_{u_2} \sim \mathcal{N}(0, \eta_u)$, $\varepsilon_{v_1} \sim \mathcal{N}(0, \eta_v)$, $\varepsilon_{v_2} \sim \mathcal{N}(0, \eta_v)$, and $\varepsilon_{v_3} \sim \mathcal{N}(0, \eta_v)$ are Gaussian noise terms with zero mean. The initial condition was set to $x_0$=(2,0,-8,8,27), which represents the starting point of the system. In the subsequent section, the sampling strategies on this system was implemented and evaluated with noise levels (NSR) at 0%, 0.1%, and 1%.

Implementing and evaluating the sampling policies: Following the same methodological process as with the previous two noisy coupled Vander Pol oscillators, the 4 sampling strategies were evaluated on the noisy coupled fast Van der Pol oscillator and noisy slow Lorenz system. FIGS. 16A-16C illustrate the performance outcomes across the same set of evaluation metrics under varying NSR levels. As the metrics and methods of evaluation are identical to those in Example 1, the same notation and interpretation are maintained FIG. 16A-16C show comparative analysis of sampling strategies on the coupled Van der Pol oscillator and slow Lorenz system.

Under noise-free conditions (NSR=0%, FIG. 16A), while the brute-force search yielded the smallest sample size of 51, it was closely followed by the uniform and greedy sampling strategies which achieved sample sizes of 55. The RL strategy, however, maintained a balance with a slightly larger sample size of 68. The RL strategy and the brute-force search achieved the smallest $\varepsilon_{SINDy}$, indicating the best fit to the true model. Notably, the greedy sampling strategy led in $\log(\kappa(\Theta))$ and $\log(tr(I))$ values, indicating the best-conditioned $\Theta$ matrix and the most informative sample set. However, the brute-force search demanded a significantly higher elapsed time. In FIG. 16B, upon introducing a low noise level (NSR=0.1%), all strategies showed an increase in $\varepsilon_{SINDy}$ and sample size, and a decrease in $\log(\kappa(\Theta))$ and $\log(tr(I))$ values. Among them, the RL approach exhibited the least increase in $\varepsilon_{SINDy}$ and sample size and the least decrease in $\log(\kappa(\Theta))$ and $\log(tr(I))$, demonstrating its robustness against noise. Despite the noise, the convergence rate for the RL strategy was 91%, significantly higher than the uniform sampling method, which fell to 1%.

When the noise level was increased to NSR=1% (FIG. 16C), every method experienced further escalation in $\varepsilon_{SINDy}$ and sample size, and a drop in $\log(\kappa(\Theta))$ and $\log(tr(I))$. The RL approach, however, retained the lowest rise in $\varepsilon_{SINDy}$ and sample size and the smallest reduction in $\log(\kappa(\Theta))$ and $\log(tr(I))$. Moreover, it had an 84% convergence rate, the highest among the strategies, while the uniform sampling method could only achieve 85%. Regarding time-related metrics at different noise levels, while the brute-force search yielded the smallest sample sizes and low $\varepsilon_{SINDy}$, it used the longest elapsed times. Conversely, the RL strategy provided a balance of relatively small sample sizes, competitive $\varepsilon_{SINDy}$, $\log(\kappa(\Theta))$, $\log(tr(I))$ values, high convergence rates, and significantly shorter elapsed times than the randomized brute-force search. To further illuminate the behavior of the sampling strategies, FIGS. 17A-17E compare the samples obtained from the RL-based policy and the randomized brute-force search—the most efficient strategy-under three noise conditions (NSR=0%, 0.1%, and 1%).

FIGS. 17A-17E show visualization of samples acquired through the RBFS and RL-based techniques for the "fast" Van der Pol oscillator coupled with the "slow" Lorenz system under distinct noise scenarios. Squares and circles in FIGS. 17A, 17C, and 17E demonstrate samples from the RL-based method and RBFS respectively, for the "fast" Van der Pol oscillator at NSR levels of 0%, 0.1%, and 1%. Similarly, FIGS. 17B, 17D, and 17F use the same symbols to showcase the "slow" Lorenz system samples under identical NSR conditions. The black trajectories were reconstructed from the simulated samples derived from solving ODEs of the multi-scale coupled system. The box depicts the high-resolution of the trajectories and samples.

Figures 17A, 17B, 17C, 17D, 17E, 17F:
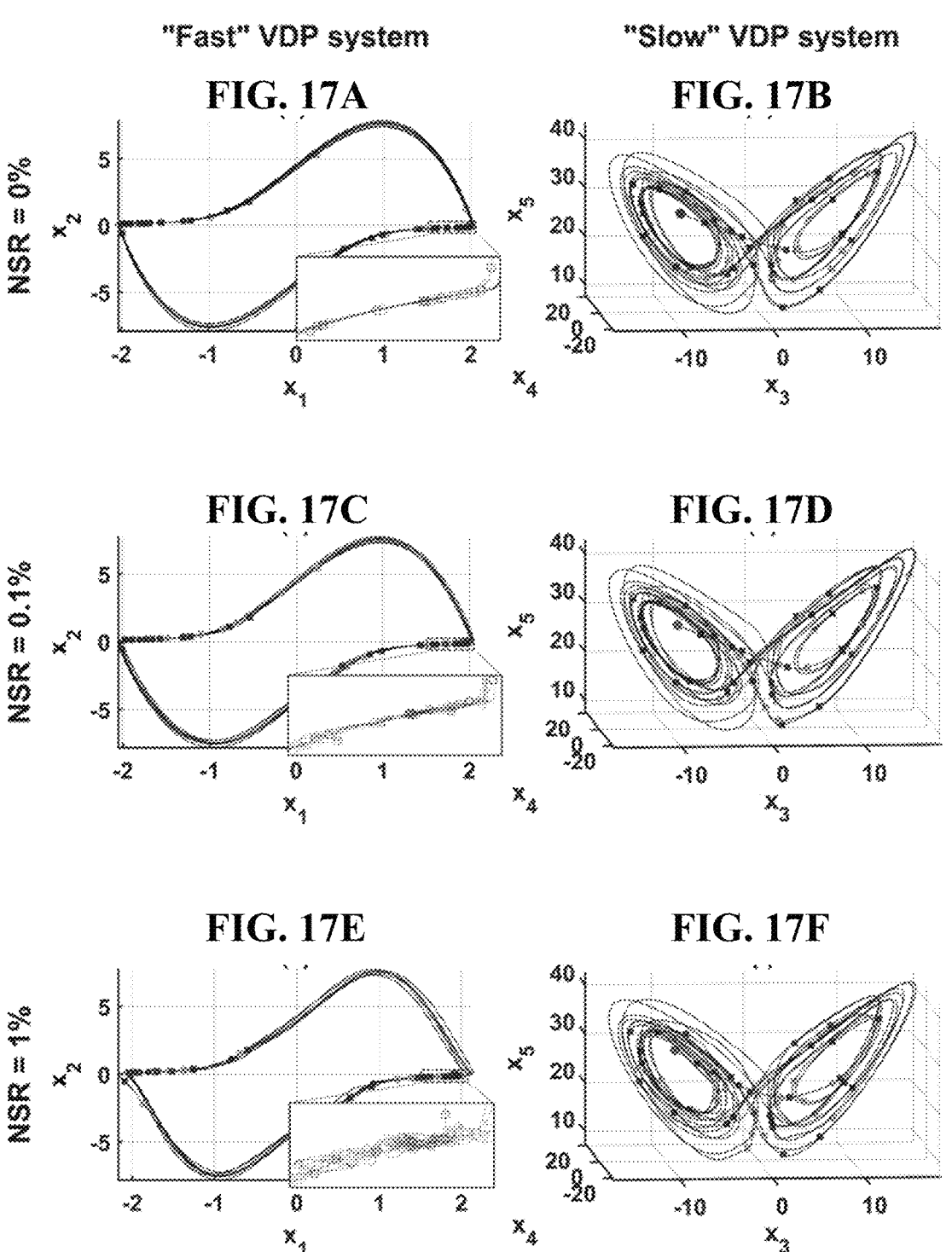
FIGS. 17A-17F show visualization of samples obtained from an example sampling strategy, where

For the noise-free scenario (NSR=0%, FIGS. 17A and 17B), both RL and RBFS strategies aligned by opting to keep the sampling period consistent. This signified a shared approach in both strategies, indicating the tendency to adapt to slower system dynamics. In FIGS. 17C and 17D, with a slight increase in noise level (NSR=0.1%), both strategies continued to uphold this decision, suggesting a common resilience against minor disturbances. This trend continued even at the higher noise level (NSR=1%, FIGS. 17E and 17F), revealing the robustness of both methods when faced with increased uncertainty. Intriguingly, there were sampling actions where the RL strategy deviated from the RBFS strategy. Under certain circumstances, the RL strategy chose to decrease the sampling period, an action that the RBFS strategy did not take. This decision underscores an extra layer of flexibility inherent to the RL strategy, highlighting its adaptability to swiftly changing system dynamics.

In this example, the VDP oscillator part of the system maintains its inherent 'limit cycle' and 'excitation' dynamics, while the slower Lorenz system adds another layer of complexity with its chaotic behavior. Notably, both the RL and RBFS strategies cleverly adapted to these dynamics. Similar to the results of the previous numerical study, in the "limit cycle" region of the VDP oscillator, the strategies used a higher sampling frequency to accurately capture the persistent oscillations. Conversely, during the "excitation" phase of the VDP oscillator, characterized by swift progression towards the limit cycle, the strategies opted for less dense sampling. The "slow" Lorenz system added further intricacy with its chaotic dynamics and slower time scale. Despite this, the RL and RBFS strategies adeptly adjusted the sampling methods to capture the complex interactions between the two systems. Both strategies continued to exhibit less intensive sampling in regions where the Lorenz system's dynamics remain relatively unchanged, while intensifying their sampling frequency in regions of chaotic behavior. As the noise scenario increased, both the RL and RBFS strategies demonstrate impressive adaptability. Despite the increased noise, the strategies maintained their characteristic frequent sampling in the limit cycle region and less dense sampling during the excitation phase of the VDP oscillator. At the same time, they adjusted their sampling methods to capture the intricate dynamics of the slower Lorenz system.

The disclosure is situated at the intersection of system identification, sampling strategy optimization, and machine learning. In the disclosure a comprehensive evaluation of various sampling strategies was conducted, specifically uniform sampling, greedy sampling. RBFS, and RL-based sampling, for SINDy algorithm when applied to noisy multi-scale coupled deterministic systems. SINDy could succinctly express the governing equations of a dynamical system from noisy data. However, their work's exploration of sampling strategies was limited, mainly employing uniform or random sampling, leaving room for further optimization. A burst sampling method was proposed for the SINDy algorithm that focused on discovering nonlinear multi-scale dynamical systems from data. The disclosure investigates the potential of deep reinforcement learning for optimizing the sampling strategy in SINDy algorithm. While \relied on more traditional mathematical approaches to sample selection, the disclosed method leverages the power of reinforcement learning to choose the most informative samples under various noise scenarios adaptively.

The comprehensive results provide us with important implications about the applicability and performance of these methods in different NSR situations. Uniform sampling emerged as an efficient strategy in terms of computational speed across all NSR scenarios. However, the downside of this method is its relative need for accuracy in generating SINDy models, as suggested by higher modeling errors. Therefore, uniform sampling might be beneficial when an approximate understanding of system dynamics is needed, but not necessarily perfect, and some degree of modeling error is tolerable. On the other hand, greedy sampling performed impressively in minimizing sample sizes, especially under noise-free conditions. This attribute can be highly beneficial when data collection is costly, time-consuming, or challenging. Nevertheless, the method's performance markedly deteriorated under noisy conditions, indicating that its applicability might be limited to ideal or controlled environments. The RBFS method employs a random yet comprehensive search across the sample space to identify critical data points at high computational cost, allowing for efficient capture of the crucial dynamics of the system. The results indicate that the RBFS method retains robust performance even in various noise conditions, making it a versatile choice for dealing with complex, real-world scenarios.

The performance comparison of the four different sampling strategies uncovers some interesting insights regarding their respective capabilities and potential application areas. Uniform sampling exhibited impressive speed in processing time across all NSR scenarios, which underscores its utility in applications where swift computation is a priority. However, it underperformed in terms of generating accurate SINDy models, as indicated by higher errors. This characteristic makes it more suitable for contexts where an immediate, although not perfect, understanding of system dynamics is desirable, and a certain degree of modeling error is tolerable. Contrastingly, greedy sampling excelled in minimizing sample sizes under noise-free conditions, an attribute that can prove beneficial in cases where data collection is costly or otherwise challenging. Despite this advantage, its efficacy noticeably declined in noisy environments. This suggests that, while the Greedy method can be highly efficient under ideal conditions, its performance might be compromised when dealing with real-world systems that often include some level of noise. Both the RL-based sampling strategy and the RBFS method stood out for their ability to better capture system dynamics, as substantiated by their lower $\log(\kappa(\Theta))$ and $\log(\mathrm{tr}(I))$ values. These metrics signify the generated samples' diversity and informativeness, and lower values indicate a more comprehensive and accurate representation of the underlying system dynamics. Therefore, these two strategies are more adept at dealing with complex or high-dimensional systems where capturing a wider range of behaviors is crucial. The RL-based sampling strategy, which is the novel contribution of the disclosed method and system, exhibited robust and efficient performance across a range of noise conditions. The RL-based sampling strategy adapts and adjusts to different scenarios, showing a robust performance, whether in the presence or absence of noise. Its key strength lies in its ability to learn and adapt to the system's dynamics, enabling it to efficiently sample crucial points in its trajectory, thus generating accurate SINDy models.

In conclusion, the disclosure contributes significantly to the field of multi-scale system identification, shedding light on the complexity of modeling such systems and the need for efficient, data-driven algorithms. a deep Q-learning based reinforcement learning framework was applied to capture this multi-scale complexity. The agent's reward signals were designed to reflect the complex dynamics, enabling the agent to sample data optimally, thereby revealing crucial multi-scale behaviors of the system. In the disclosed methodology, Sparse Identification of Nonlinear Dynamics (SINDy) played a key role in discovering and predicting system dynamics. The disclosed framework was assessed in two numerical studies: (1) the coupled fast and slow Van der Pol oscillator, and (2) a noisy fast Van der Pol oscillator coupled with a noisy slow Lorenz system. In each scenario, the reinforcement learning model showcased its ability to autonomously determine the optimal data sampling strategy to capture the multi-scale dynamics effectively. Importantly, the learned policy was intricate, assisting in addressing challenges of non-convergence, reducing the sample size, and improving SINDy's robustness to noise. These results constitute a significant advancement in the development of data-efficient reinforcement learning methods for multi-scale complex systems. The potential implications of the disclosure extend beyond system identification, with potential applications in diverse fields where understanding and manipulating complex system dynamics are paramount. By facilitating a more accurate understanding and efficient control of these systems, the disclosure paves the way for future advancements in multi-scale modeling.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

What is claimed is:

1. A method for obstructive sleep apnea detection comprising:
   obtaining a white noise contaminated sensor signal for a patient;
   extracting a feature based on the white noise contaminated sensor signal;
   determining a matrix based on the feature;
   determining an intermittent forcing signal based on the matrix;
   determining an overcomplete representation of the intermittent forcing signal; and
   generating an obstructive sleep apnea indication based on the overcomplete representation and a threshold.

2. The method of claim 1, wherein the white noise contaminated sensor data comprises an electrocardiogram signal.

3. The method of claim 1, wherein the obtaining of the white noise contaminated sensor signal comprises:
   receiving a sensor signal; and
   adding white noise in the sensor signal for the white noise contaminated sensor signal.

4. The method of claim 1, further comprising:
   determining a level of the white noise to make the intermittent forcing signal a Gaussian distribution.

5. The method of claim 1, wherein the feature comprises a heart rate variability feature to quantify time intervals between adjacent heartbeats.

6. The method of claim 1, wherein the matrix comprises a window length of the feature and a number of points in a trajectory of the feature.

7. The method of claim 1, further comprising:
   determining a burst duration and an inter-burst duration between two adjacent burst durations; and
   determining an obstructive sleep apnea characteristic for the patient based on the burst duration and the inter-burst duration.

8. The method of claim 7, wherein the two adjacent burst durations comprise a first burst duration and a second burst duration, and
   wherein the inter-burst duration comprises a duration between an end time of the first burst duration and a starting time of the second burst duration.

9. The method of claim 1, wherein the overcomplete representation is determined by applying a continuous wavelet transform to the intermittent forcing signal.

10. The method of claim 9, wherein the continuous wavelet transform is defined as:

$$X_w(a, b) = \frac{1}{|a|^{1/2}} \int_{-\infty}^{\infty} v_r(t) \bar{\psi}\left(\frac{t-b}{a}\right) dt,$$

where $X_w$ is the continuous wavelet transform, $\psi(t)$ is a continuous mother wavelet function and $\bar{\psi}$ is a complex conjugate, a is a scale, b is a translational value, and $v_r(t)$ is the intermittent forcing signal.

11. The method of claim 10, wherein the threshold is defined as:
   $|X_w(a,b)| \geq \psi_{CWT} \max|X_w(a,b)|$, where $\psi_{CWT}$ is a tuning parameter.

12. The method of claim 1, wherein the obstructive sleep apnea indication comprises a binary indication indicative of normal breathing or disordered breathing.

13. The method of claim 1, further comprising:
   receiving a sensor signal;
   determining multi-scale system dynamics; and
   adaptively sampling the sensor signal based on the multi-scale system dynamics for the white noise contaminated sensor signal.

14. A system for obstructive sleep apnea detection comprising:
   a memory; and
   a processor communicatively coupled to the memory;
   wherein the memory stores a set of instructions which, when executed by the processor, causes the processor to:
      obtain a white noise contaminated sensor signal for a patient;
      extract a feature based on the white noise contaminated sensor signal;
      determine a matrix based on the feature;
      determine an intermittent forcing signal based on the matrix;
      determine an overcomplete representation of the intermittent forcing signal; and
      generate an obstructive sleep apnea indication based on the overcomplete representation and a threshold.

15. The system of claim 14, wherein the white noise contaminated sensor data comprises an electrocardiogram signal.

16. The system of claim 14, wherein the feature comprises a heart rate variability feature to quantify time intervals between adjacent heartbeats.

17. The system of claim 14, wherein the overcomplete representation is determined by applying a continuous wavelet transform to the intermittent forcing signal.

18. The system of claim 17, wherein the continuous wavelet transform is defined as:

$$X_w(a, b) = \frac{1}{|a|^{1/2}} \int_{-\infty}^{\infty} v_r(t) \overline{\psi}\left(\frac{t-b}{a}\right) dt,$$

where $X_w$ is the continuous wavelet transform, $\psi(t)$ is a continuous mother wavelet function and $\overline{\psi}$ is a complex conjugate, a is a scale, b is a translational value, and $v_r(t)$ is the intermittent forcing signal.

19. The system of claim 18, wherein the threshold is defined as:

$|X_w(a,b)| \geq \psi_{CWT} \max |X_w(a,b)|$, where $\psi_{CWR}$ is a tuning parameter.

20. The system of claim 14, wherein the set of instructions further causes the processor to:

receive a sensor signal;

determine multi-scale system dynamics; and adaptively sample the sensor signal based on the multi-scale system dynamics for the white noise contaminated sensor signal.

* * * * *